(12) United States Patent
Lin et al.

(10) Patent No.: US 7,101,902 B2
(45) Date of Patent: Sep. 5, 2006

(54) 2-GUANIDINYLIMIDAZOLIDINEDIONE COMPOUNDS AND METHODS OF MAKING AND USING THEREOF

(75) Inventors: Ai Jeng Lin, North Potomac, MD (US); Quan Zhang, Montgomery County, MD (US); Jian Guan, Montgomery County, MD (US); Wilbur K. Milhous, Germantown, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/992,363

(22) Filed: Nov. 19, 2004

(65) Prior Publication Data

US 2005/0148645 A1    Jul. 7, 2005

Related U.S. Application Data

(60) Provisional application No. 60/523,670, filed on Nov. 21, 2003.

(51) Int. Cl.
*A61K 31/4168* (2006.01)
*C07D 233/48* (2006.01)

(52) U.S. Cl. .................................. 514/390; 548/318.1
(58) Field of Classification Search ............. 548/318.1; 514/390
See application file for complete search history.

(56) References Cited

U.S. PATENT DOCUMENTS 4,957,936 A * 9/1990 Nakamura et al. .......... 514/389

OTHER PUBLICATIONS

Corcoran et al., American Journal of Tropical Medicine and Hygiene, (1993), 49(4), pp. 473-477.*
Corcoran et al. (1993) "Causal Prophylactic and Radical Curative Activity of WR182393 (A Guanylhydrazone) Against *Plasmodium cynomolgi* in *Macaca mulatta*" Am. J. Trop. Med. Hyg. 49(4):473-477.
Covell et al. (1949) "'Paludrine' (Proguanil) in Prophylaxis and Treatment of Malarial Infections caused by a West African Strain of *P. falciparum*" British Med. J. 1:88-91.
Curd et al. (1945) "Studies on Synthetic Antimalarial Drugs: Some Biguanide Derivatives as New Types of Antimalarial Substances with Both Therapeutic and Causal Prophylactic Activity" Annals of Trop. Med. And Parasit. 39:208-216.
Shanks et al. (2001) "A New Primaquine Analogue Tafenoquine (WR 238605), for Prophylaxis against *Plasmodium falciparum* Malaria" Clin. Infect. Diseases 33:1968-1974.
PCT Search Report and Written Opinion for PCT/US04/38909, mailed Oct. 11, 2005.

* cited by examiner

*Primary Examiner*—Laura L. Stockton
(74) *Attorney, Agent, or Firm*—Elizabeth Arwine

(57) ABSTRACT

Disclosed herein are 2-guanidinylimidazolidinedione compounds having the structural formula A or B wherein $R^1$ and $R^2$ are each independently a hydrogen, halogen, alkyl, alkoxyl, amino, alkylamino or aralkyl, and wherein $R^3$ is an alkyl, cycloalkyl, heterocycloalkyl, acyl, aryl, heteroaryl, alkylaryl, sulfonyl, alkylsulfonyl, and pharmaceutically acceptable salts thereof, and methods of making thereof. Also disclosed are methods of treating, preventing, or inhibiting malaria with the 2-guanidinylimidazolidinedione compounds, and pharmaceutical compositions comprising the 2-guanidinylimidazolidinedione compounds, and kits.

34 Claims, 1 Drawing Sheet

2-GUANIDINYLIMIDAZOLIDINEDIONE COMPOUNDS AND METHODS OF MAKING AND USING THEREOF

CROSS REFERENCE TO RELATED APPLICATIONS

This application claims the benefit of U.S. Provisional Patent Application No. 60/523,670, filed 21 Nov. 2003, listing Ai J. Lin, Quan Zhang, Jian Guan, and Wilbur K. Milhous as inventors, which is herein incorporated by reference in its entirety.

ACKNOWLEDGMENT OF GOVERNMENT SUPPORT

This invention was made by employees of the United States Army. The government has rights in the invention.

BACKGROUND OF THE INVENTION

1. Field of the Invention

The present invention relates to 2-guanidinylimidazolidinedione compounds, methods of making and purifying 2-guanidinylimidazolidinedione compounds, and methods of using the 2-guanidinylimidazolidinedione compounds to prevent, treat, or inhibit malaria in a subject.

2. Description of the Related Art

The current global situation with respect to malaria indicates that about two billion people are exposed to the disease and of these 400 million people are already infected. See Trigg, P. I., and A. V. Kondrachine (1998) The Current Global Malaria Situation, Chapter 2, p. 11–22, in MALARIA PARASITE BIOLOGY, PATHOGENESIS AND PROTECTION. Ed. I. W. Sherman, ASM Press, Washington, D.C. Each year between 100 to 200 million new cases of infection are reported and approximately 1 to 2 million people die due to malaria. The situation is rapidly worsening mainly due to non-availability of effective drugs and development of drug resistance of a large number of non-immune people in areas where malaria is frequently transmitted. See White, N.J. (1998) Br. Med. Bull. 54:703–715.

WR182393 is a mixture of cyclic dicarboxamide derivatives of chlorproguanil (1), the latter of which is highly active against primary exoerythrocytic forms of

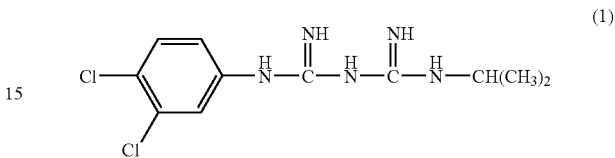

Plasmodium falciparum and P. vivax. See Covell, G. et al. (1949) British Medical Journal 1:88–91; and Curd, F. S. H. et al. (1945) Annals of Tropical Medicine and Parasitology 39:208–216. The compound was synthesized first by Werbel et al. in 1972 and later by Starks Associates Co. by reacting chloroguanil (1) with diethyl oxalate (2)

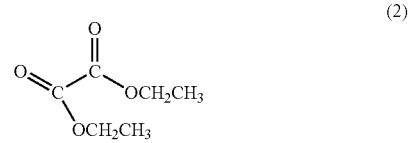

according to the following Scheme 1:

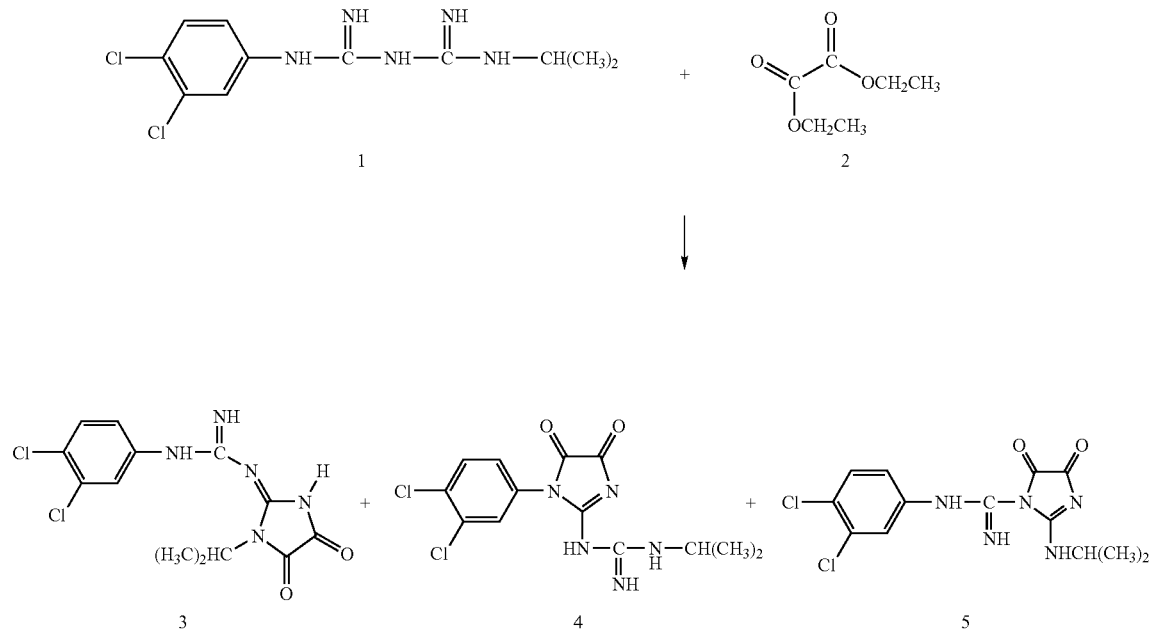

-continued

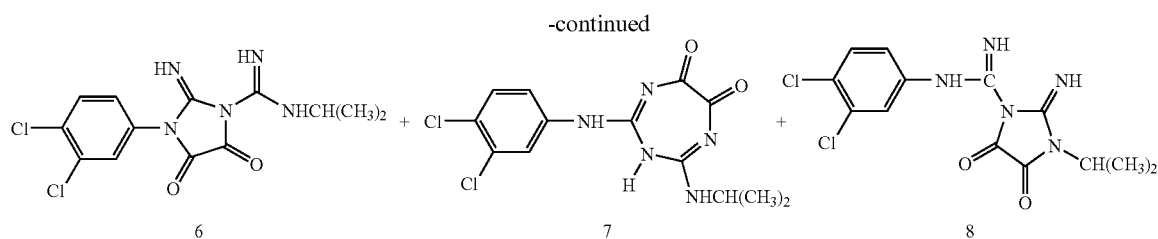

6    7    8

Recently, WR182393 was found to possess prophylactic activity in the mouse Rane assay comparable to that of tafenoquine when administered subcutaneously. In the Rane mouse prophylactic assay, WR182393 demonstrated radical cure by subcutaneous administration at 10 mg/kg and at higher doses of 160 mg/kg by oral. See Corcoran, K D, et al. (1993) Am. J. Trop. Med. Hyg. 49:473–477, and Shanks, G D, et al. (2001) Clinical Infectious Diseases 33:1968–1974. In Rhesus monkeys, WR182393 also demonstrated both radical curative and causal prophylactic activity against *P. cynomolgi* when given i.m. Thus, the active component of WR182393 is potentially a valuable lead for drug discovery of a causal prophylactic drug for prevention of *falciparum* malaria.

Due to poor solubility of the products in water or organic solvents, the purification of the reaction mixture is very difficult. The structure of the reaction product was assumed by the manufacture to be compound 3.

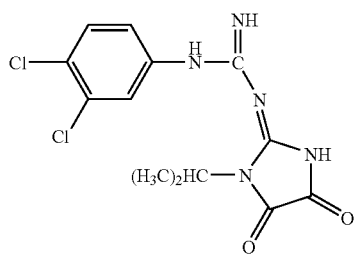

(3)

However, there was no analytical data to support this contention. Because of the poor solubility, small-scale purification of the mixture is very difficult and large-scale purification is almost impossible. Consequently, the structure determination of the components of WR182393 mixtures has been a frustrating task of medicinal chemists.

Therefore, a need still exists for methods for making and purifying the active compounds of WR182393 and compositions thereof that may be used for treating, preventing, or inhibiting malaria.

SUMMARY OF THE INVENTION

The present invention provides 2-guanidinylimidazolidinedione compounds and compositions and methods of making and using thereof.

In some embodiments, the present invention provides a compound having the structural formula A or B wherein $R^1$ and $R^2$ are each independently a hydrogen, halogen, alkyl, alkoxyl, or arakyl, and wherein $R^3$ is an alkyl, cycloalkyl, heterocycloalkyl, aryl, heteroaryl, alkylaryl, sulfonyl, or alkylsulfonyl, or a pharmaceutically acceptable salt thereof. In some preferred embodiments, $R^1$ and $R^2$ are each independently —H, —Cl, —Br, —CF₃, —OCH₃, or —OCF₃. In some preferred embodiments, $R^3$ is —CH₂CH₃, —CH₂CH(CH₃)₂, —C(CH₃)₃, —CH₂C₆H₅, —(CH₂)₅CH₃,

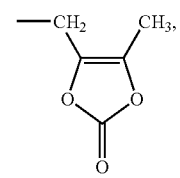

—CH₂CH₂C=CH₂, or —CH₂CH₂OCH₂C₆H₅. In some preferred embodiments, the compound is N-(3,4-dichlorophenyl)-N'-(1-isopropyl-4,5-dioxoimidazolidin-2-ylidene)guanidine (3); N-(3,4-dichlorophenyl)-N'-ethoxycarbonyl-N"-(1-isopropyl-4,5-dioxo-imidazolidin-2-ylidene)-guanidine (3a); N-(3,4-dichlorophenyl)-N'-(isobutoxycarbonyl)-N"-(1-isopropyl-4,5-dioxo-imidazolidin-2-ylidene)-guanidine (3b); N-(3,4-dichlorophenyl)-N'-(1-isopropyl-4,5-dioxoimidazolidin-2-ylidene)-N"-(tert-butoxycarbonyl)-guanidine (3c); N-(3,4-dichlorophenyl)-N'-(benzyloxycarbonyl)-N"-(1-isopropyl-4,5-dioxo-imidazolidin-2-ylidene)-guanidine (3d); N-(3,4-dichlorophenyl)-N'-(1-hexyloxycarbonyl)-N"-(1-isopropyl-4,5-dioxo-imidazolidin-2-ylidene)-guanidine (3e); N-(3,4- dichloro-phenyl)-N'-(5-methyl-2-oxo-1,3-dioxol-4-yl) methyl-N''-(1-isopropyl-4,5-dioxo-imidazolidin-2-ylidene) guanidine (3f); N-(3,4-dichlorophenyl)-N'-(3-butenyloxycarbonyl)-N''-(1-isopropyl-4,5-dioxoimidazolidin-2-ylidene)-guanidine (3g); N-(3,4-dichloro-phenyl)-N'-(2-benzyloxyethoxycarbonyl)-N''-(1-isopropyl-4,5-dioxo-imidazolidin-2-ylidene)-guanidine (3h); N-[1-(3,4-dichlorophenyl)-4,5-dioxo-4,5-dihydro-1H-imidazol-2-yl]-N'-isopropylguanidine (4); N-[1-(3,4-dichlorophenyl)-4,5-dioxo-imidazolidin-2-ylidene]-N'-isopropyl-N''-(ethylcarbonyl)guanidine (4a); N-[1-(3,4-dichlorophenyl)-4,5-dioxo-imidazolidin-2-ylidene]-N'-isopropyl-N''-(isobutyloxycarbonyl)guanidine (4b); N-[1-(3,4-dichlorophenyl)-4,5-dioxo-imidazolidin-2-ylidene]-N'-isopropyl-N''-(tert-butoxycarbonyl)guanidine (4c); N-[1-(3,4-dichlorophenyl)-4,5-dioxo-imidazolidin-2-ylidene]-N'-isopropyl-N''-(benzyloxycarbonyl)guanidine (4d); N-[1-(3,4-dichlorophenyl)-4,5-dioxo-imidazolidin-2-ylidene]-N'-isopropyl-N''-(1-hexyloxycarbonyl)guanidine (4e); or N-[1-(3,4-dichlorophenyl)-4,5-dioxo-imidazolidin-2-ylidene]-N'-isopropyl-N''-(3-butenyloxycarbonyl)guanidine (4g).

In some embodiments, the present invention provides a method of treating, preventing, or inhibiting malaria or a disease or disorder associated with malaria or a *Plasmodium* parasite which comprises administering a therapeutically effective amount of at least one compound of the present invention to a subject in need thereof. The subject is a mammal, preferably human. In some embodiments, the compound is administered intramuscularly, orally, or transdermally. In some embodiments, the method further comprises administering to the subject a supplementary active compound such as an antimalarial, an antiproliferative agent, an antifungal agent, an antibacterial, or an anti-inflammatory agent. In some preferred embodiments, the compound is N-(3,4-dichlorophenyl)-N'-(1-isopropyl-4,5-dioxoimidazolidin-2-ylidene)guanidine (3); N-(3,4-dichlorophenyl)-N'-ethoxycarbonyl-N''-(1-isopropyl-4,5-dioxo-imidazolidin-2-ylidene)-guanidine (3a); N-(3,4-dichlorophenyl)-N'-(isobutoxycarbonyl)-N''-(1-isopropyl-4,5-dioxo-imidazolidin-2-ylidene)-guanidine (3b); N-(3,4-dichlorophenyl)-N'-(1-isopropyl-4,5-dioxoimidazolidin-2-ylidene)-N''-(tert-butoxycarbonyl)-guanidine (3c); N-(3,4-dichlorophenyl)-N'-(benzyloxycarbonyl)-N''-(1-isopropyl-4,5-dioxo-imidazolidin-2-ylidene)-guanidine (3d); N-(3,4-dichlorophenyl)-N'-(1-hexyloxycarbonyl)-N''-(1-isopropyl-4,5-dioxo-imidazolidin-2-ylidene)-guanidine (3e); N-(3,4-dichloro-phenyl)-N'-(5-methyl-2-oxo-1,3-dioxol-4-yl) methyl-N''-(1-isopropyl-4,5-dioxo-imidazolidin-2-ylidene) guanidine (3f); N-(3,4-dichlorophenyl)-N'-(3-butenyloxycarbonyl)-N''-(1-isopropyl-4,5-dioxoimidazolidin-2-ylidene)-guanidine (3g); N-(3,4-dichloro-phenyl)-N'-(2-benzyloxyethoxycarbonyl)-N''-(1-isopropyl-4,5-dioxo-imidazolidin-2-ylidene)-guanidine (3h); N-[1-(3,4-dichlorophenyl)-4,5-dioxo-4,5-dihydro-1H-imidazol-2-yl]-N'-isopropylguanidine (4); N-[1-(3,4-dichlorophenyl)-4,5-dioxo-imidazolidin-2-ylidene]-N'-isopropyl-N''-(ethylcarbonyl)guanidine (4a); N-[1-(3,4-dichlorophenyl)-4,5-dioxo-imidazolidin-2-ylidene]-N'-isopropyl-N''-(isobutyloxycarbonyl)guanidine (4b); N-[1-(3,4-dichlorophenyl)-4,5-dioxo-imidazolidin-2-ylidene]-N'-isopropyl-N''-(tert-butoxycarbonyl)guanidine (4c); N-[1-(3,4-dichlorophenyl)-4,5-dioxo-imidazolidin-2-ylidene]-N'-isopropyl-N''-(benzyloxycarbonyl)guanidine (4d); N-[1-(3,4-dichlorophenyl)-4,5-dioxo-imidazolidin-2-ylidene]-N'-isopropyl-N''-(1-hexyloxycarbonyl)guanidine (4e); or N-[1-(3,4-dichlorophenyl)-4,5-dioxo-imidazolidin-2-ylidene]-N'-isopropyl-N''-(3-butenyloxycarbonyl)guanidine (4g).

In some embodiments, the present invention provides a method for making N-(3,4-dichlorophenyl)-N'-(1-isopropyl-4,5-dioxoimidazolidin-2-ylidene)guanidine (3) which comprises reacting N-(3,4-dichlorophenyl)guanidine with 1-isopropyl-2-methylsulfanyl-1H-imidazole-4,5-dione. In some embodiments, the method further comprises preparing N-(3,4-dichlorophenyl)guanidine by adding $NH_4OH$ to 1-(3,4-dichlorophenyl)-2-methylisothiourea HI salt in ethanol to obtain a solution, refluxing the solution, removing the solvent to obtain a residue, and obtaining N-(3,4-dichlorophenyl)guanidine. In some embodiments, the method further comprises preparing 1-isopropyl-2-methylsulfanyl-1H-imidazole-4,5-dione by adding iodomethane to isopropyl thiourea in dry acetone, obtaining the hydroiodide salt, obtaining a suspension of the hydroiodide salt, adding triethylamine to the suspension, adding oxalyl chloride to the suspension, and obtaining N-(3,4-dichlorophenyl)guanidine by crystallization.

In some embodiments, the present invention provides a method for making a compound having the structural formula A of the present invention, which comprises treating a compound having the structural formula a

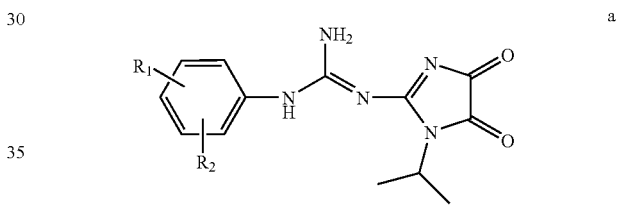

a with an alkyl chloroformate having the structural formula x

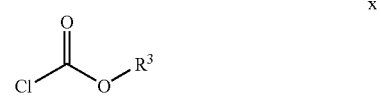

x under the catalysis of triethylamine or a dialkyldicarbonate having the structural formula y

y under the catalysis of dimethylaminopyridine (DMAP), wherein $R^1$ and $R^2$ are each independently a hydrogen, halogen, alkyl, alkoxyl, or arakyl, and wherein $R^3$ is an alkyl, cycloalkyl, alkoxycarbonyl, heterocycloalkyl, acyl, aryl, heteroaryl, alkylaryl, sulfonyl, or alkylsulfonyl. In some embodiments, $R^1$ and $R^2$ are each independently —H, —Cl, —Br, —$CF_3$, —$OCH_3$, or —$OCF_3$. In some embodiments, $R^3$ is —$CH_2CH_3$, —$CH_2CH(CH_3)_2$, —$C(CH_3)_3$, —$CH_2C_6H_5$, —$(CH_2)_5CH_3$,

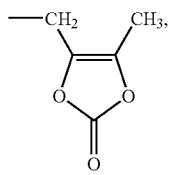

—CH$_2$CH$_2$C=CH$_2$, or —CH$_2$CH$_2$OCH$_2$C$_6$H$_5$.

In some embodiments, the present invention provides a method for making N-[1-(3,4-dichlorophenyl)-4,5-dioxo-4,5-dihydro-1H-imidazol-2-yl]-N'-isopropyl-guanidine (4) which comprises reacting 1-(3,4-dichlorophenyl)-2-methylsulfanyl-1H-imidazole-4,5-dione with isopropylguanidine, or acid hydrolysis of N-[1-(3,4-dichlorophenyl)-4,5-dioxo-imidazolidin-2-ylidene]-N'-isopropyl-N''-(tert-butoxycarbonyl)guanidine. In some embodiments, N-[1-(3,4-dichlorophenyl)-4,5-dioxo-imidazolidin-2-ylidene]-N'-isopropyl-N''-(tert-butoxycarbonyl)guanidine is prepared by reacting 1-(3,4-dichlorophenyl)-2-methylsulfanyl-1H-imidazole-4,5-dione with N-isopropyl-N'-(tert-butoxycarbonyl)guanidine. In some embodiments, 1-(3,4-dichlorophenyl)-2-methylsulfanyl-1H-imidazole-4,5-dione is prepared by adding methyl oxalyl chloride to a solution of 1-(3,4-dichlorophenyl)-2-methylisothiourea and triethylamine in dry CH$_2$Cl$_2$. In some embodiments, N-isopropyl-N'-(tert-butoxycarbonyl)guanidine is obtained by adding a solution of di-tert-butyldicarbonate in CHCl$_3$ to a solution of isopropylguanidine in DMF.

In some embodiments, the present invention provides a method for making the compound having the structural formula B of the present invention, which comprises treating a compound having the structural formula b

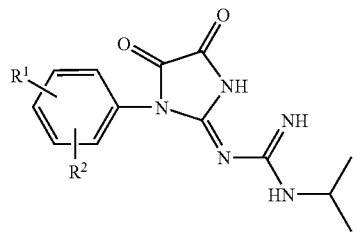

with an alkyl chloroformate having the structural formula x

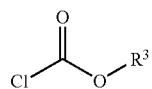

under the catalysis of triethylamine or a dialkyldicarbonate having the structural formula y

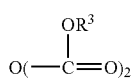

under the catalysis of dimethylaminopyridine (DMAP), wherein R$^1$ and R$^2$ are each independently a hydrogen, halogen, alkyl, alkoxyl, or alkylaryl, and wherein R$^3$ is an alkyl, cycloalkyl, heterocycloalkyl, acyl, aryl, heteroaryl, alkylaryl, sulfonyl, or alkylsulfonyl. In some embodiments, R$^1$ and R$^2$ are each independently —H, —Cl, —Br, —CF$_3$, —OCH$_3$, or —OCF$_3$. In some embodiments, R$^3$ is —CH$_2$CH$_3$, —CH$_2$CH(CH$_3$)$_2$, —C(CH$_3$)$_3$, —CH$_2$C$_6$H$_5$, —(CH$_2$)$_5$CH$_3$,

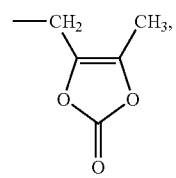

—CH$_2$CH$_2$C=CH$_2$, or —CH$_2$CH$_2$OCH$_2$C$_6$H$_5$.

In some embodiments, the present invention provides a pharmaceutical composition comprising at least one compound of having the structural formula A or B of the present invention and a pharmaceutically acceptable excipient. In some embodiments, the pharmaceutical composition further comprises a supplementary active compound such as an antimalarial, an antiproliferative agent, an antifungal agent, an antibacterial, or an anti-inflammatory agent. In some embodiments, the pharmaceutical composition comprises N-(3,4-dichlorophenyl)-N'-(1-isopropyl-4,5-dioxoimidazolidin-2-ylidene)guanidine (3) or N-[1-(3,4-dichlorophenyl)-4,5-dioxo-4,5-dihydro-1H-imidazol-2-yl]-N'-isopropylguanidine (4).

In some embodiments, the present invention provides kits comprising at least one compound of the present invention packaged together with instructional material. The kits may further comprise a device for administering the compound to a subject, reagents for assaying whether the subject is in need of the compound, e.g. assay for determining whether the subject has malaria or has been exposed to a *Plasmodium* parasite, supplementary active compounds such as antimalarials, antiproliferative agents, antifungal agents, antibacterials, or anti-inflammatory agents. In some embodiments, the compounds are packaged as single dose amounts. More than one single dose package may be present in one kit.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

Figure 1:
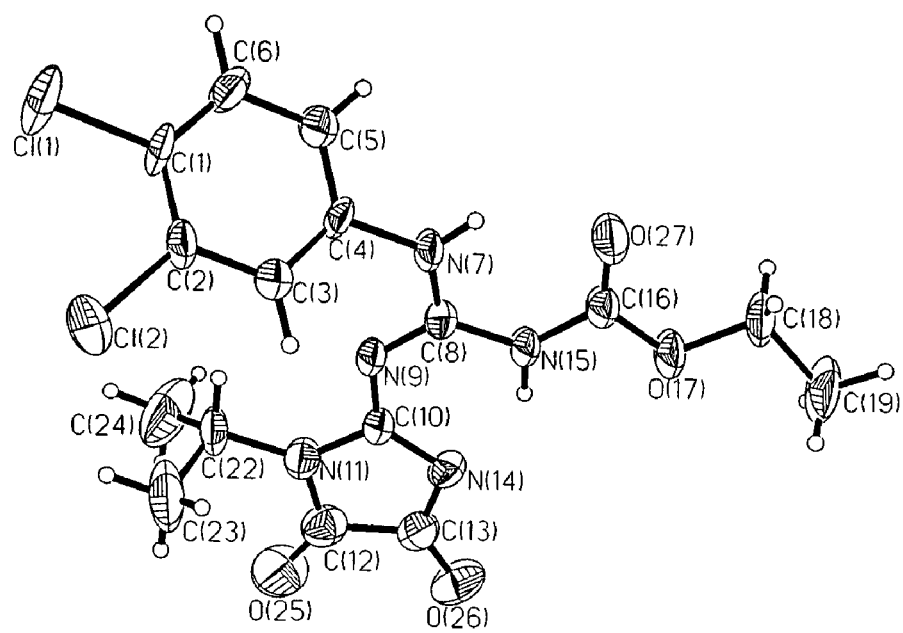
FIG. 1 is a thermal ellipsoid plot of crystalline N-(3,4-dichlorophenyl)-N'-ethylcarbonyl-N''-(1-isopropyl-4,5-dioxo-imidazolidin-2-ylidene)-guanidine (3a).

DETAILED DESCRIPTION OF THE INVENTION
The procedure used to synthesize WR182393 by Werbel et al. and Starks Associates, Buffalo, N.Y. (a U.S. Army contractor) involved treatment of chlorproguanil (1) with diethyl oxalate (2), a reaction which gave a mixture of six possible closely related products as shown in the following Scheme 1:
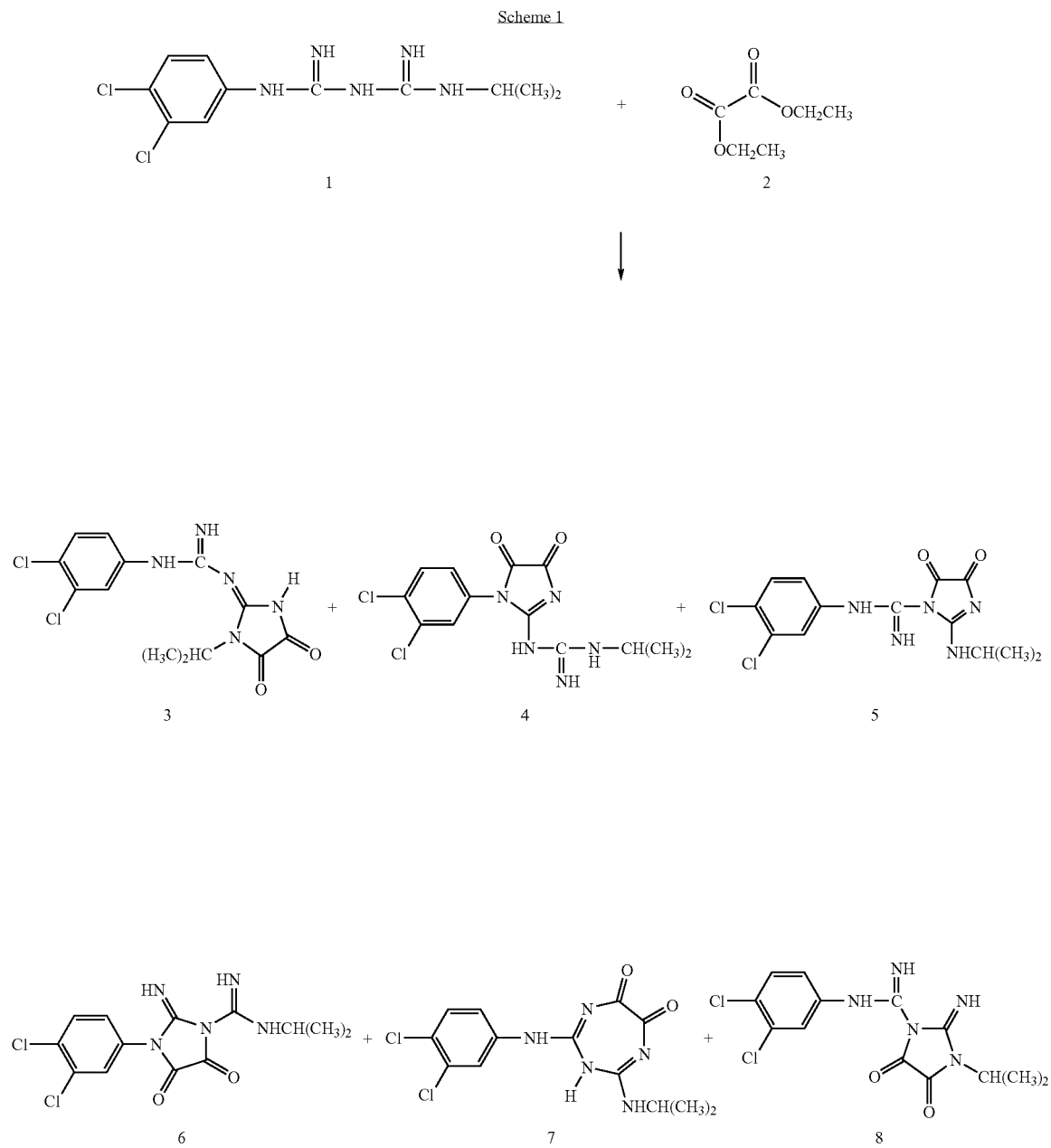

TLC and NMR data showed that the WR182393 sample prepared by Starks Co. comprised at least two compounds selected from the six proposed products, compounds 3–8 and the starting material 1.

As part of an ongoing project to search for effective causal prophylactic drugs against malaria, the active components of WR182393 have now been successfully purified and identified as compounds 3 and 4 and the starting material compound 1.

The purification process involved the carbamate formation of WR182393 mixtures to give adducts with improved solubility in organic solvents, and thus facilitated the separation, purification and identification of the components. See Scheme 2.

isomer A (1.3 g, 27%). The structure of the two products was determined by NMR and x-ray crystallography as 3a (isomer A) and 4a (isomer B).

Ethyl carbamate 3a: m.p. 181° C. $^1$H NMR (CDCl$_3$, 600 Hz) δ 13.20 (s, 1H), 11.20 (s, 1H), 7.84 (d, J=2.4 Hz, 1H), 7.53 (d, J=8.6 Hz, 1H), 7.24 (dd, J=8.6 Hz, J=2.4 Hz, 1H), 4.45 (m, 1H), 4.38 (q, J=7.1 Hz, 2H), 1.43 (t, J=7.1 Hz, 3H), 1.40 (d, J=7.0 Hz, 6H). Anal. (C$_{16}$H$_{17}$N$_5$O$_4$Cl$_2$) C, H, N.

Compound 3a was also prepared from pure component 3, provided herein.

Ethyl carbamate 4a: m.p. 257° C. $^1$H NMR (CDCl$_3$, 600 Hz) δ 7.56 (d, J=2.4 Hz, 1H), 7.55 (d, J =8.3 Hz, 1H), 7.29

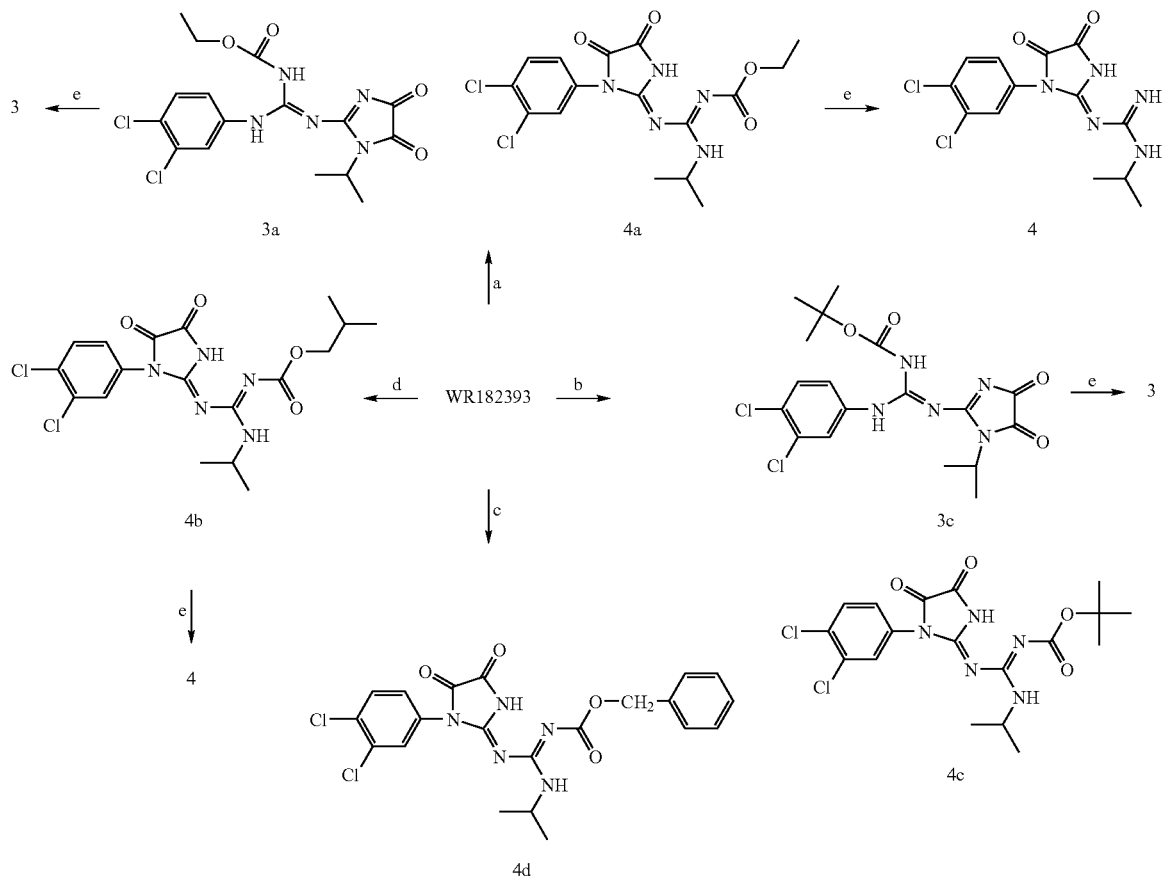

a). ClOCOEt, Et$_3$N, CHCl$_3$, b). di-t-butyl-dicarbonate, DMAP, CHCl$_3$, c). dibenzyldicarbonate, DMAP, DMF,
d). ClOCOCH$_2$CH(CH$_3$)$_2$, Et$_3$N, CHCl$_3$, e). 3N HCl/EtoAc Procedure for Preparing Ethyl Carbamates 3a and 4a: To a suspension of WR182393 (4 g, 11.7 mmol) in CHCl$_3$ (80 ml) was treated with Et$_3$N (6.2 ml, 4 equiv) and ethyl chloroformate (4.4 ml, 4 equiv). The reaction mixture was stirred at room temperature overnight, washed with water and the chloroform layer was dried over Na$_2$SO$_4$ and concentrated. The residue was applied to silica gel flash chromatography and eluted with 2.5% ethyl acetate/chloroform. The ethylcarbamate obtained (2.8 g) was a combination of two isomers (1.7:1/isomer A: isomer B) as indicated by NMR. Fractional crystallization of the mixture from ethylacetate gave first isomer B (850 mg, 18%), followed by (dd, J=2.4 Hz, J=8.3 Hz, 1H), 4.32 (q, J=7.1 Hz, 2H), 4.16 (m, 1H), 1.39 (t, J=7.1 Hz, 3H), 1.25 (d, J=6.6 Hz, 6H). Anal. (C$_{16}$H$_{17}$N$_5$O$_4$Cl$_2$) C, H, N.

Compound 4a was also prepared from pure compound 4, provided herein.

X-Ray Crystal Structure Determination of 3a and 4a: The x-ray samples were colorless plates (3a: 0.7×0.35×0.12 mm; 4a: 0.45×0.42×0.06 mm) crystallized from methanol. Data collection was performed at room temperature (293±2 K) on a Bruker P4 diffractometer using Cu Kα radiation and a graphite monochrometer in the incident beam. Reflections used to refine the unit cell parameters by least squares methods are as follows: 3a, 31 reflections in the range of 12°≦θ≦40°; 4a, 27 reflections in the range of 14°≦θ≦26°. Crystal data 3a: $C_{16}H_{17}C_{12}N_5O_4$, FW=414.25, Monoclinic, P2(1)/n, a=14.919(2) Å, b=7.613(1) Å, c=17.504(3) Å, β=102.79(2)°, V=1938.7(5) Å$^3$, Z=4. Crystal data 4a: $C_{16}H_{17}C_{12}N_5O_4$, FW=414.25, Triclinic, P-1, a=7.924(2) Å, b=9.704(2) Å, c=13.375(2) Å, α=102.90(1)°, β=96.18(1)°, γ=97.39(2)°, V=984.2(4) Å$^3$, Z=4.

The data were collected using the ω scan technique with a variable scan rate ranging from 3°/min minimum to 60°/min maximum depending upon the intensity of the reflection. Three reflections were checked as intensity controls every 97 reflections and remained constant within 3.2% for 3a, 3.5% for 4a. No absorption correction was applied. The structures were solved using direct methods. See Karle, J. & Karle, I. L. (1966) Acta. Crystallogr. 21:849–859; Sheldrick, G. M. (1985) "Crystallographic Algorithms for Mini and Maxi Computers" IN CRYSTALLOGRAPHIC COMPUTING, Sheldrick, G. M., Krüger, C. Goddard, R., Eds., Oxford University Press: Oxford Vol. 3, pages 175–179; Sheldrick, G. M. (1990) SHELXTL software; University of Göttingen, Federal Republic of Germany, which are herein incorporated by reference. Full matrix least-squares refinement was performed on coordinates and anisotropic thermal parameters for the nonhydrogen atoms, isotropic thermal parameters for the hydrogen atoms using reflections for which $|F_0|>4\sigma(F_0)$. Hydrogen atoms H7 and H15 for 3a and H114 and H23 for 4a were located in the difference maps. The remaining hydrogen atoms were placed in idealized positions, and during refinement, the coordinates of these hydrogen atoms rode with the coordinates of the carbon to which they are attached. Final bond distances and angles were all within expected and acceptable limits.

FIG. 1 is a thermal ellipsoid plot of crystalline N-(3,4-dichlorophenyl)-N'-ethylcarbonyl-N''-(1-isopropyl-4,5-dioxo-imidazolidin-2-ylidene)-guanidine (3a), showing the atom numbering scheme used for the x-ray crystallographic data. Atoms N7, C8, N9, C10, N11, C12, C13, N14, N15, C16, O17, O25, O26, and O27 are essentially co-planar with atom N7 showing the largest deviation (0.13 Å) off a least-squares plane through these atoms. The phenyl ring is angled such that the C3-C4-N7-C8 torsion angle is 52.8°. The crystal structure contained only intramolecular hydrogen bonds, between N7-H7 and O27 and N15-H15 and N14. The N7-H7 . . . O27 angle is 131.1°, H7 . . . O27 distance is 2.029 Å, and N7 . . . O27 distance is 2.674 Å The N15-H15 . . . N14 angle is 139.8°, H15 . . . N14 distance is 1.879 Å, and N15 . . . N14 distance is 2.660 Å.

Figure 2:
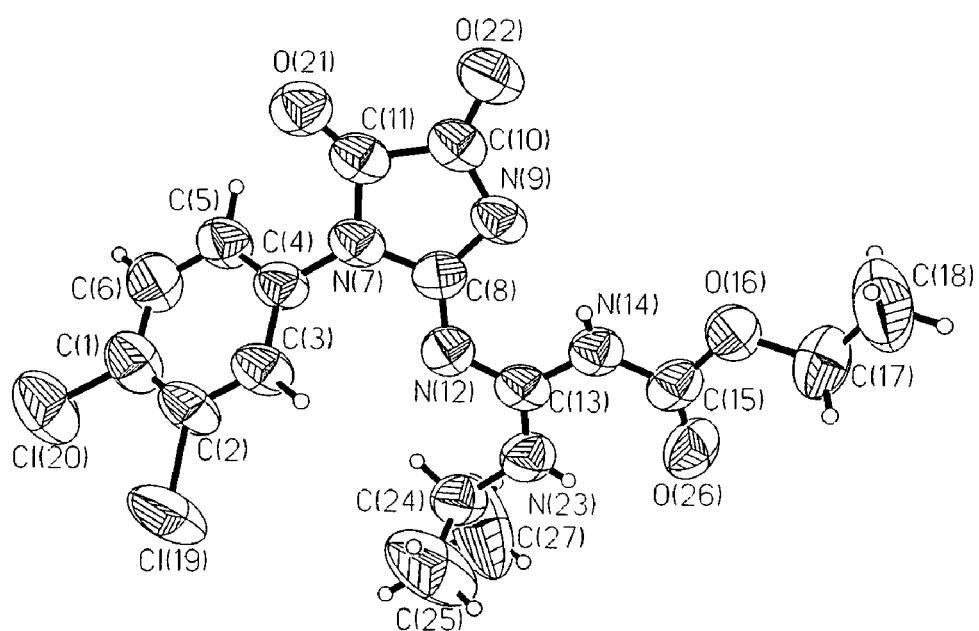
FIG. 2 is a thermal ellipsoid plot of crystalline N-[1-(3,4-dichlorophenyl)-4,5-dioxo-imidazolidin-2-ylidene]-N'-isopropyl-N''-(ethylcarbonyl)guanidine (4a).

FIG. 2 is a thermal ellipsoid plot of crystalline N-[1-(3,4-dichlorophenyl)-4,5-dioxo-imidazolidin-2-ylidene]-N'-isopropyl-N''-(ethylcarbonyl)guanidine (4a), showing the atom numbering scheme used for the x-ray crystallographic data. Atoms N7, C8, N9, C10, C11, N12, C13, N14, C15, O16, O21, O22, N23, and O26 are essentially co-planar with atoms O16 and O22 showing the largest deviations (0.14 Å) off a least-squares plane through these atoms. The phenyl ring is angled such that the C3-C4-N7-C8 torsion angle is 50.7°. The crystal structure contained only intramolecular hydrogen bonds, between N14-H14 and N7 and N23-H23 and O26. The N14-H14 . . . N9 angle is 148.7°, H14 . . . N9 distance is 1.966 Å, and N14 . . . N9 distance is 2.653 Å. The N23-H23 . . . O26 angle is 129.8°, the H23 . . . O26 distance is 2.077 Å, and N23 . . . O26 distance is 2.679 Å. The large thermal ellipsoids for the terminal methyl groups indicate that these methyl groups are not tightly sterically restricted in the crystalline packing Procedure for Preparing t-Butyl Carbamates 3c and 4c: To a suspension of WR182393 (500 mg, 1.46 mmol) in DMF (10 ml) was added DMAP (18 mg, 0.2 equiv) and di-tert-butyl dicarbonate (1.27 g, 4 equiv). The reaction mixture was stirred at room temperature overnight and partitioned in chloroform/H$_2$O. The organic layer was successively washed with brine and water, dried with NaSO$_4$, filtered and concentrated. The crude products were purified by silica gel flash chromatography (2.5% ethyl acetate/chloroform) and crystallized from ethyl acetate to give pure isomer A (3c) (54 mg, 26%) and isomer B (4c) in about equal yield.

t-Boc carbamate 3c: m.p. 223° C. $^1$H NMR (CDCl$_3$, 600 Hz) δ 7.84 (d, J=2.3, 1H), 7.52 (d, J=8.6, 1H), 7.25 (dd, J=8.6, J=2.3, 1H), 4.44 (m, 1H), 1.60 (s, 9H), 1.39 (d, J=6.0 Hz, 6H). Anal. (C$_{18}$H$_{21}$N$_5$O$_4$Cl$_2$) C, H, N.

t-Boc carbamate 4c: m.p. 227° C. $^1$H NMR (CDCl$_3$, 300 Hz) δ 7.55 (d, J=2.3 Hz, 1H), 7.54 (d, J=8.6 Hz, 1H), 7.27 (dd, J=2.3 Hz, J=8.6 Hz, 1H), 4.15 (m, 1H), 1.53 (s, 9H), 1.22 (d, J=6.6 Hz, 6H). Anal. (C$_{18}$H$_{21}$N$_5$O$_4$Cl$_2$) C, H, N.

Compound 3c and 4c were also made from pure compound 3 and 4, instead of the mixture WR182393 as provided herein.

Hydrolysis of carbamate: t-Boc carbamate (3c) (196 mg, 0.44 mmol) was dissolved in 3M HCl-EtOAc (3 ml). After 2 hours, the mixture was neutralized with saturated NaHCO$_3$ and filtered. The yellow solid was washed successively with water and chloroform to yield pure 3 (140 mg, 93%).

Compound 3: m.p. 230° C. $^1$H NMR (DMSO-d6, 600 Hz) δ 7.78 (d, J=2.2 Hz, 1H), 7.69 (d, J=8.6 Hz, 1H), 7.31 (dd, J=8.6 and 2.2 Hz), 4.39 (m, 1H), 1.33 (d, J=6.7 Hz, 6H). $^{13}$C NMR: δ 172.24, 170.65, 162.14, 160.08, 132.13, 131.76, 126.96, 125.00, 44.44, 20.54. IR: 3277, 3140, 1752, 1725, 1553, 1464, 1317, 996, 808, 754 cm$^{-1}$.Anal. (C$_{13}$H$_{13}$N$_5$O$_2$Cl$_2$) C, H, N.

Compound 3 is identical to the sample prepared by the method of the present invention according to Scheme 3 as follows:

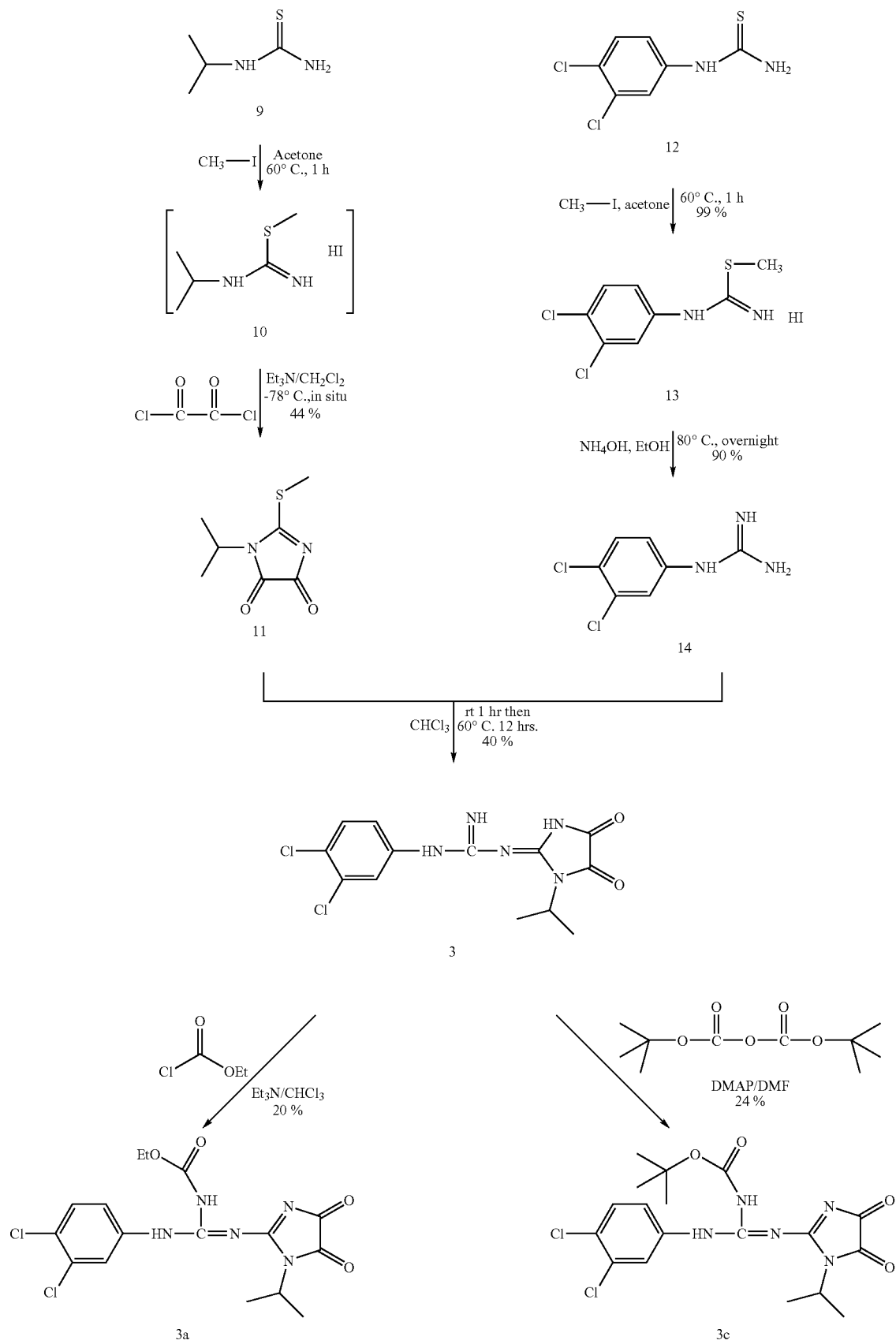

Compound 4 was also prepared by the hydrolysis of 4b under the same conditions as above and by the method of the present invention according to the following Scheme 4, yield 89%, m.p. 244° C. NMR and IR spectrum of compound 4 prepared by the two different methods are identical.
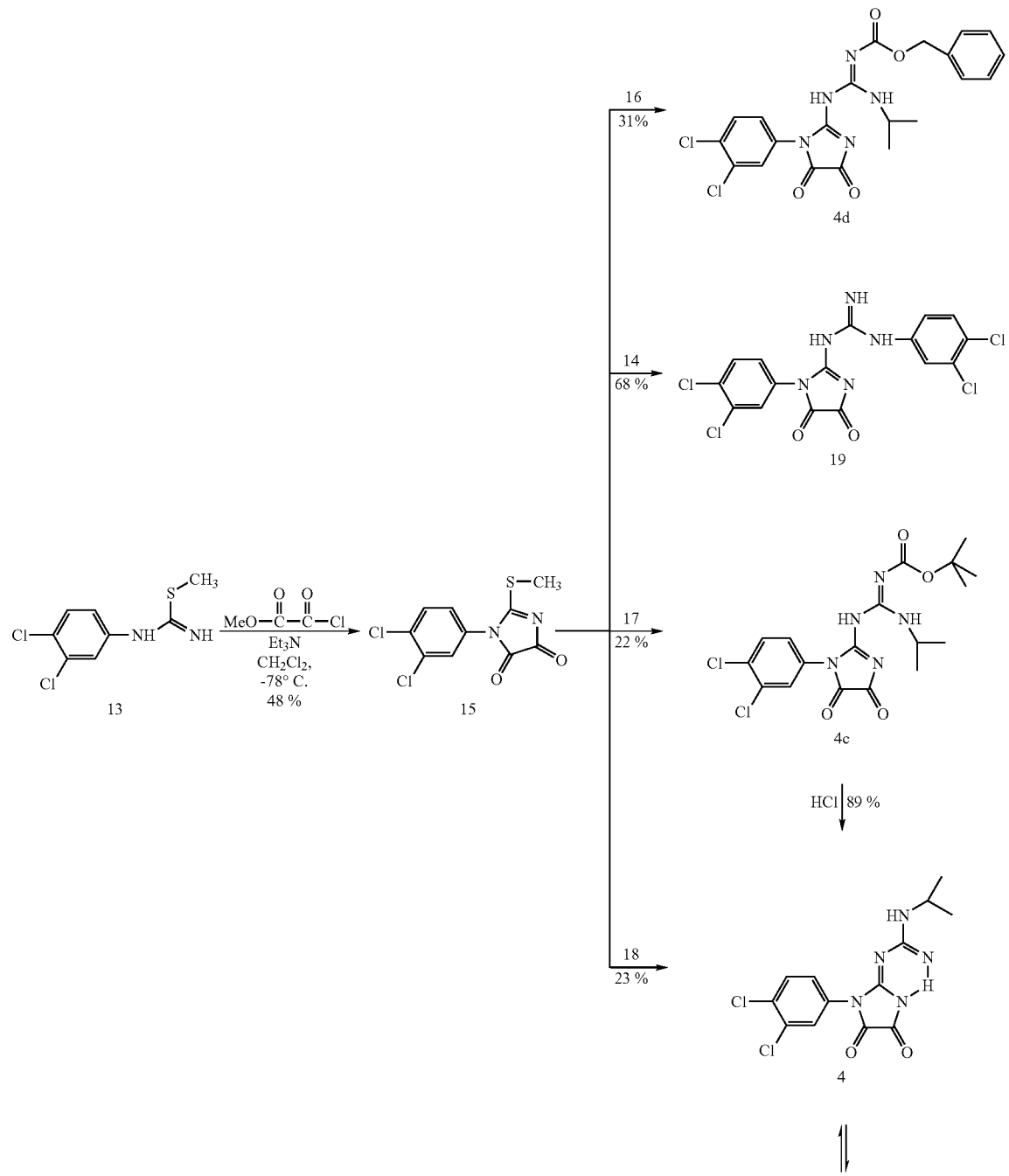
Scheme 4

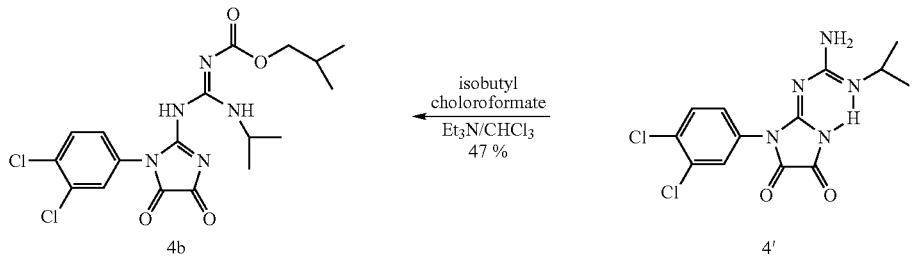

It should be noted that the prior art method for the preparation of compounds 3 and 4 gave a mixture which is extremely difficult to be purified. Thus, the prior art method is not a practical procedure even in laboratory scale. The present invention provides a facile and unambiguous method for the preparation and purification of the active 2-guanidinylimidazolidinedione compounds of the WR182393 mixture, compounds 3 and 4 and derivatives thereof. Several carbamate derivatives of compounds 3 and 4 were prepared and found to possess profound causal prophylactic antimalarial activity against *P. yoelii* in sporozoites challenged mouse model by oral administration (see Table 4 and 5). Two of the carbamates 3c and 4b were found to possess protective activity in Rhesus monkeys at 10 and 30 mg/kg by intramuscular administration (see Table 8). Therefore, the present invention also provides methods for treating, preventing, or inhibiting malaria in a subject which comprises administering a therapeutically effective amount of at least one 2-guanidinylimidazolidinedione compound of the present invention.

The approach for synthesis of compound 3 involved heating of N-(3,4-dichlorophenyl)guanidine (14) and 1-isopropyl-2-methylsulfanyl-1H-imidazole-4,5-dione (11) in chloroform overnight to furnish the yellowish product in 40% yield. See Scheme 3; and see also Linney, Ian D., et al. (1965) J. Med. Chem. 43:2362–2370, which is herein incorporated by reference. The intermediate 11 was obtained in two steps by methylation of isopropylthiourea 9 with methyl iodide to generate S-methylisothiouronium 10 followed by treatment of 10 with oxalyl chloride under the catalysis of triethylamine to give 11 in 44% yield See Ulrich, Henri, et al. (1965) J. Org. Chem. 30(8):2781–2783, and Stoffel, P. J. (1964) J. Org. Chem. 29:2794–2796, which are herein incorporated by reference. Likewise, the synthesis of 3,4-dichlorophenylguanidine (14) involved the methylation of 3,4-dichlorophenylthiourea 12 with CH₃I to give the corresponding S-methylthiouronium salt 13 followed by amination to give 14 in 90% yield.

Compound 4 was synthesized by a similar procedure for the preparation of compound 3 as shown in Scheme 4. N-isopropyl-N'-(tert-butoxycarbonyl)guanidine 17, was obtained in good yield by treatment of isopropylguanidine (18) with di-tert-butyldicarbonate as shown in the following Scheme 5:

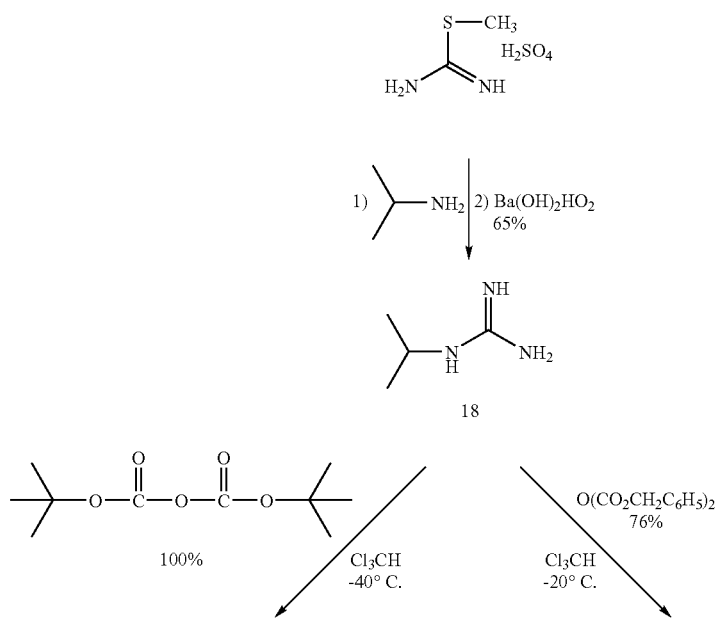

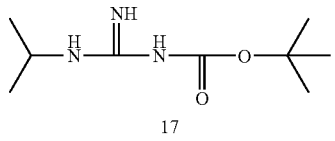
17

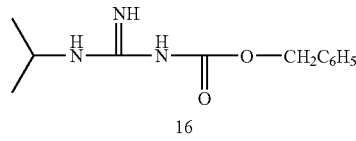
16

Compound 18 was prepared, in turn, by amination of commercially available product, S-methylisothiouronium sulfate, followed by conversion of the isopropylguanidine salt to free base 18 by treatment with Ba(OH)$_2$. See Pressman, Berton C. (1963) J. Biol. Chem. 238(1):401–409, which is herein incorporated by reference. The other intermediate 16, N-(benzyloxycarbonyl)-N'-isopropylguanidine, was prepared by treatment of 18 with dibenzyl dicarbonate. See Scheme 5.

Compound 4 was prepared either by direct reaction of compound 15 with isopropylguanidine (18) or with t-Boc isopropylguanidine (17) followed by acid hydrolysis of the t-Boc carbamate 4c. These two approaches gave a similar total yield and the two products are identical in melting point, IR and NMR spectrum. Since t-Boc carbamate 4c is soluble in organic solvent and that isopropylguanidine (18) is much more soluble in water than in organic solvent, carbamate 4c is much easier to handle and gave better yield than using guanidine 18. Compound 15, the key intermediate, was produced in good yield by treatment of S-methylthiouronium 13 with methyl oxalylchloride in CH$_2$Cl$_2$ under Et$_3$N catalysis at −78° C. The carbamates 4, 4d, 4c and 19 were prepared by the same procedure, treating intermediate 15 with compound 18, 16, 17 and 14, respectively, as shown in Scheme 4.

Although the NMR spectra of compound 3 in CDCl$_3$ showed a pure single compound, the NMR spectra of compound 4 indicated the existence of two tautomers 4 and 4' with ratio of about 3 to about 1, as indicated by the integration of two sets of doublets resonance at 1.15 and 1.09 ppm for the methyl protons of the isopropyl group. See Katritzky, Alan R., et al. (2000) J. Org. Chem. 65:8080–8082, which is herein incorporated by reference.

Chemistry

Melting points were determined on a Mettler FP62 melting point apparatus and are uncorrected. Unless otherwise noted, all non-aqueous reactions were performed under an oxygen-free atmosphere of nitrogen with rigid exclusion of moisture from reagents and glassware. Analytical thin layer chromatography (TLC) was performed using HPTLC-HLF normal phase 150 microns silica gel plates (Analtech, Newark, Del.). Visualization of the developed chromatogram was performed by UV absorbance, or spreading with aqueous potassium permanganate, or ethanolic anisaldehyde. Liquid chromatography was performed using a Horizon HPFC System (Biotage, Charlottesville, Va.) with Flash 25M or 40M cartridges (KP-Sil™ Silica, 32–63 μm, 60 Å). Preparative TLC was performed using silica gel GF Tapered Uniplates (Analtech, Newark, Del.). Infrared spectra were recorded on a Bio-Rad FTS 3000 spectrophotometer (Bio-Rad Laboratories, Cambridge, Mass.) and are reported in reciprocal centimeters (cm$^{-1}$). $^1$H NMR and $^{13}$C NMR spectra were recorded in deuteriochloroform, unless otherwise noted, on a Bruker Avance 300 and Bruker Avance 600 spectrometer (Bruker Instruments, Inc, Wilmington, Del.). Chemical shifts are reported in parts per million on the δ scale from an internal standard of tetramethylsilane. Combustion analyses were performed by Atlantic Microlab, Inc. (Norcross, Ga.). Where analyses are indicated by symbols of the elements, the analytical results obtained were within +/− 0.4% of the theoretical values. When necessary, solvents and reagents were dried as follows: ether, tetrahydrofuran, benzene, and toluene were stored and distilled from sodium benzophenone ketyl; dichloromethane, triethylamine, pyridine, and hexane were distilled over calcium hydride. Unless otherwise stated, the reagents were purchased from Fisher Scientific, Aldrich Chemical Company, Lancaster, or Fluka, and used as received.

1-Isopropyl-2-methylsulfanyl-1H-imidazole-4,5-dione (11): Isopropyl thiourea 9 (8.0 g, 67.7 mmol) in 100 ml of dry acetone was added iodomethane (6.3 ml, 101 mmol) dropwise at room temperature. After the addition was completed, the mixture was refluxed for 1 hour, and the solvent was evaporated to dryness under the reduced pressure to give a gum. The gummy hydroiodide salt was suspended in 200 ml of dry methylene chloride and to the suspension was added triethylamine (37.7 ml, 270 mmol). The mixture was stirred for 30 minutes at room temperature, cooled down to −78° C. with a dry ice/acetone bath. To the mixture was added dropwise oxalyl chloride (40.6 ml of 2M solution, 81.2 mmol) and stirred at −78° C. for 1 hour. The reaction was quenched by addition of water to decompose the excess oxalyl chloride, the solvent was dried over Na$_2$SO$_4$ and evaporated to dryness in vacuo.

Recrystallization of the solid product with CHCl$_3$/hexanes mixed solvents yielded intermediate 11 as a yellow needle (7.3 g, 58%), mp 193.5° C. $^1$H NMR (600 MHz, CDCl$_3$): δ 4.19 (m, 1H), 2.76(s, 3H), 1.48 (d, J=6.6 Hz, 6H); $^{13}$C NMR: δ 191.64, 167.18, 158.49, 48.62, 20.06, 14.64; IR: 1759, 1740, 1450, 1303, 1050 cm$^{-1}$. MS (m/z): 172, 144, 83. Anal. (C$_7$H$_{10}$N$_2$O$_2$S): C, H, N, S.

1-(3,4-dichlorophenyl)-2-methylisothiourea (13): To a solution of 3,4-dichlorophenylthiourea (5.00 g, 22.61 mmol) in 80 ml of anhydrous acetone was added iodomethane (2.11 ml, 33.92 mmol) and the resultant solution was heated at reflux for 1 hour. The solvent was removed under reduced pressure, and the residue was suspended in EtOAc. The white solid product was collected, washed with fresh solvent and dried in vacuo to give hydroiodide salt (8.119 g, 22.37 mmol, 99%) as a white solid, mp 160° C. $^1$H NMR (600 MHz, DMSO-d$_6$): δ 7.80 (d, J=8.6 Hz, 1H), 7.75 (d, J=2.4 Hz, 1H), 7.37 (dd, J=8.6 and J=2.4 Hz, 1H), 2.78 (s, 3H); $^{13}$C NMR: δ 170.64, 136.24, 132.94, 132.63, 131.68, 128.95, 123.19. IR: 1628, 1576, 1541, 1464, 1306, 1124 cm$^{-1}$. Anal. (C$_8$H$_9$Cl$_2$IN$_2$S): C, H, Cl, N, S.

To the water solution of 1-(3,4-dichlorophenyl)-2-methylisothiourea hydroiodide was added saturated Na$_2$CO$_3$ solution at ice cold temperature till the pH reached about 9 to about 10. The reaction mixture was extracted with CHCl$_3$ three times. The chloroform extracts were combined and dried over Na$_2$SO$_4$. The solvent was removed in vacuo to give crude product (13) as a white solid in quantitative yield, mp 166° C. The product was pure enough for further reaction. $^1$H NMR (600 MHz, CDCl$_3$) δ 7.34(d, J=8.4 Hz, 1H), 7.02 (d, J=2.4 Hz, 1H), 6.75 (dd, 8.4 and 2.4 Hz, 1H), 4.58 (s, 2H), 2.42 (s, 3H); $^{13}$C NMR: δ 157.14, 148.74, 133.24, 131.31, 126.80, 124.23, 122.09, 14.16.

N-(3,4-dichlorophenyl)guanidine (14): To the solution of 13 (2.29 g, 6.31 mmol) in 23 ml of ethanol was added 6.87 ml of NH$_4$OH. The reaction mixture was stirred at room temperature for 10 minutes, and the clear solution was refluxed for 12 hours. The solvent was removed under reduced pressure and the residue was suspended in saturated Na$_2$CO$_3$ solution. The solid was collected, washed sequentially with H$_2$O and Et$_2$O and dried to give the title compound as a white solid (1.16 g, 90%), mp 208° C. $^1$H NMR (600 MHz, DMSO-d$_6$): δ 7.39 (d, J=8.6 Hz, 1H), 7.02 (d, J=2.4 Hz, 1H), 6.79 (dd, J=8.6 and 2.4 Hz, 1H), 5.79 (br s, 3H); $^{13}$C NMR: δ 155.38, 130.69, 130.28, 124.30, 123.50. IR: 1684, 1624, 1559, 1472, 1380, 1328, 869, 818, 671 cm$^{-1}$. MS (m/z): 204 (M$^+$), 187, 162, 127, and 90.

1-(3,4-dichlorophenyl)-2-methylsulfanyl-1H-imidazole-4,5-dione (15): The reaction solution of 1-(3,4-dichlorophenyl)-2-methylisothiourea (13) (6.6 g, 28.3 mmol) and triethylamine (7.5 ml, 56.5 mmol) in 200 ml of dry CH$_2$Cl$_2$ was cooled down to −78° C. with an acetone/dry ice bath. To the solution was added dropwise methyl oxalyl chloride (5.2 ml, 56.5 mmol). The resulting brown reaction mixture was stirred at −78° C. for 2 hours and quenched with water. The mixture was extracted with CHCl$_3$ three times and the CHCl$_3$ extracts were combined, dried over Na$_2$SO$_4$ and evaporated to dryness under the reduced pressure. The crude product was purified by recrystallization with hexanes/CHCl$_3$/CH$_2$Cl$_2$ mixed solvent to yield 15 as yellow crystals (4.0 g, 16.12 mmol, 48%). $^1$H NMR (300 MHz, CDCl$_3$): δ 7.63 (d, J=8.7 Hz, 1H), 7.46 (d, J=2.4 Hz, 1H), 7.20 (dd, J=8.7 and 2.4 Hz, 1H), 2.76 (s, 3H); $^{13}$C NMR: δ 179.00, 158.00, 135.14, 134.19, 129.97, 131.67, 129.07, 126.36, 14.44. MS (m/z): 289 (M$^+$), 286, 187, 159, and 124. Anal. (C$_{10}$H$_6$Cl$_2$O$_2$S) C. H. Cl. N.

N-(benzyloxycarbonyl)-N'-isopropylguanidine (16): To the solution of isopropylguanidine (18, 0.50 g, 4.95 mmol) in DMF (20 ml) was added with stirring at −20° C. a solution of dibenzyl dicarbonate (0.644 g, 2.25 mmol) in 20 ml of CHCl$_3$. The mixture was stirred for additional two hrs after the addition was completed and allowed to stir at room temperature overnight. After being quenched with water, the mixture was extracted with CHCl$_3$, washed with water (4×100 ml) and dried over Na$_2$SO$_4$. The solvent was removed under reduced pressure to afford the product as a colorless crystal (0.4 g, 1.702 mmol, 76%). $^1$H NMR (300 MHz, CDCl$_3$) δ 7.40–7.25 (m, 5H), 5.08 (s, 2H), 3.57 (m, 1H), 1.22 (d, J=6.0 Hz, 6H); $^{13}$C δ 163.80, 160.47, 137.33, 128.17, 127.62, 127.45, 66.05, 43.20, 22.63.

N-isopropyl-N'-(tert-butoxycarbonyl)guanidine (17): To the solution of isopropylguanidine (1.33 g, 13.17 mmol) in DMF (30 ml) was added in small portions at room temperature solution of di-tert-butyl dicarbonate (1.435 g, 6.584 mmol) in 40 ml of CHCl$_3$ and the reaction mixture was stirred at room temperature overnight. After quenched with water (20 ml), the mixture was extracted with CHCl$_3$ three times. The chloroform extracts were combined and washed with water (4×50 ml) and dried over Na$_2$SO$_4$. The solvent was evaporated to dryness under reduced pressure to afford the pure crude product as a colorless liquid (1.32 g, 6.58 mmol, 100%). The crude product was used for further reactions without purification. $^1$H NMR (300 MHz, CDCl$_3$): δ 3.51 (m, J=6.3 Hz, 1H), 1.43 (s, 9H), 1.20(d, J=5.3 Hz, 6H); $^{13}$C NMR: δ 63.81, 160.49, 77.84, 43.16, 29.70, 22.88.

Isopropylguanidine (18): The solution of S-methylisothiourea sulfate (65.9 g, 250 mmol) in water (100 ml) was cooled with an ice/salt bath. To the solution was added isopropylamine (42.5 ml, 500 mmol) dropwise with stirring. The reaction mixture was allowed to stir at room temperature for 16 hours after the addition of amine was completed and was then refluxed for about 4 to about 5 hours. The solution was evaporated to dryness under the reduced pressure and the residue was crystallized from 95% EtOH, to give isopropylguanidine sulfate as colorless needles (16.12 g, 81.01 mmol, 32%). $^1$H NMR (300 MHz, D$_2$O): δ 3.72 (m, 1H), 1.27 (d, J=6.4 Hz, 6H); $^{13}$C NMR: δ 158.45, 46.50, 24.11; IR: 1675, 1623, 1071 cm$^{-1}$.

The isopropylguanidine sulfate was converted to free base by addition of Ba(OH)$_2$H$_2$O and the barium sulfate formed was removed by centrifugation to give free base (18) as a colorless viscous gel in 65% yield. $^1$H NMR (300 MHz, D$_2$O): δ 3.64 (m, 1H), 1.17 (d, J=6.5 Hz, 6H). $^3$C NMR: δ 46.34, 24.10.

N-(3,4-dichlorophenyl)-N'-[1-(3,4-dichlorophenyl)-4,5-dioxo-imidazolidin-2-ylidene]-guanidine (19): To the solution of the crude dione 15 (0.551 g, 1.907 mmol) in 25 ml of dry CHCl$_3$ was added N-(3,4-dichlorophenyl)guanidine (14) (0.389 g, 1.907 mmol) at room temperature. The reaction mixture was heated at 50° C. overnight. The solid was collected and washed sequentially with CHCl$_3$ and H$_2$O to afford the compound 19 as a light yellow solid (0.573 g, 1.288 mmol, 68%), mp 220° C. $^1$H NMR (300 MHz, DMSO-d$_6$): δ 7.75(d, J=8.3 Hz, 1H), 7.69 (s, 1H), 7.55–7.40 (m, 3H), 7.15 (d, 7.9 Hz, 1H); $^{13}$C NMR: δ 170.54, 169.33, 160.26, 156.74, 136.75, 132.72, 131.15, 131.00, 130.73, 130.52, 129.64, 128.04. MS (m/z) 444 (MH$^+$), 256, 227, 185. Anal. (C$_{16}$H$_9$Cl$_4$N$_5$O$_2$) C, H, Cl, N.

N-(3,4-dichlorophenyl)-N'-(1-isopropyl-4,5-dioxoimidazolidin-2-ylidene)guanidine (3): To the solution of dione 11 (0.712 g, 3.83 mmol) in 80 ml of dry CHCl$_3$ was added guanidine 14 (0.74 g, 3.64 mmol) and the reaction mixture was heated in an oil-bath at 50° C. for 16 hours. The solid precipitates were collected, washed sequentially with H$_2$O, CH$_3$OH and CHCl$_3$ to afford the compound 3 as a light yellow solid (0.497 g, 40%). mp 233° C. $^1$H NMR (600 MHz, DMSO-d$_6$): δ 7.77 (d, J=2.2 Hz, 1H), 7.68 (d, J=8.6 Hz, 1H), 7.31 (dd, J=8.6 and 2.2 Hz, 1H), 4.38 (m, 1H), 1.33 (d, J=6.7 Hz, 6H). $^{13}$C NMR: δ 172.24, 170.65, 162.14, 160.08, 132.13, 131.76, 126.96, 125.00, 44.44, 20.54. IR: 3277, 3140, 1752, 1725, 1553, 1464, 1317, 996, 808, 754 cm$^{-1}$. Anal. (C$_{13}$H$_{13}$Cl$_2$N$_5$O$_2$): C, 45.63; H, 3.83; N, 19.94. Found: C, 45.40; H, 3.71; N, 19.94.

N-(3,4-dichlorophenyl)-N'-ethoxycarbonyl-N''-(1-isopropyl-4,5-dioxo-imidazolidin-2-ylidene)-guanidine (3a): To the mixture of N-(3,4-dichlorophenyl)-N'-(1-isopropyl-4,5-dioxo-imidazolidin-2-ylidene)-guanidine (3, 0.050 g, 0.146 mmol) in CHCl$_3$ (5 ml) was added, at room temperature, first Et$_3$N (63 μl, 0.045 mmol) and then ethyl chloroformate (42 μl, 0.44 mmol). The reaction mixture was further stirred at room temperature overnight. After being quenched with water, the mixture was extracted with CHCl$_3$, dried over Na$_2$SO$_4$, and evaporated to dryness. The residue was purified by flush silica gel column chromatography using about 2% to about 5% ethyl acetate in CHCl$_3$ as eluent to furnish 3a as a white solid (0.0121 g, 20%), mp 180° C.: $^1$H NMR (300 MHz, CDCl$_3$): δ 13.20 (s, 1H), 11.20 (s, 1H), 7.80 (d, J=2.5 Hz, 1H), 7.54 (d, J=8.6 Hz, 1H), 7.21 (dd, J=8.6 and 2.5 Hz, 1H), 4.45 (m, 1H), 4.38 (q, J=7.1 Hz, 2H), 1.43 (t, J=7.1 Hz, 3H), 1.41 (d, J=7.0 Hz, 6H); $^{13}$C NMR: δ 173.40, 168.26, 160.28, 155.89, 154.65, 134.25, 133.06, 131.12, 130.67, 126.44, 123.22, 64.16, 45.35, 19.95, 14.14. Anal. (C$_{16}$H$_{17}$N$_5$O$_4$Cl$_2$), C, H, N.

N-(3,4-dichlorophenyl)-N'-(isobutoxycarbonyl)-N"-(1-isopropyl-4,5-dioxo-imidazolidin-2-ylidene)-guanidine (3b): Compound 3b was prepared by the same method for preparation of 3a, using pure compound 3 (1.400 g, 4.094 mmol) and isobutyl chloroformate to yield compound 3b as a pale yellow solid (1.162 g, 2.629 mmol, 64%). $^1$H NMR (300 MHz, CDCl$_3$) δ 13.10 (s, 1H), 11.13 (s, 1H), 7.81 (d, J=2.5 Hz, 1H), 7.50 (d, J=8.6 Hz, 1H), 7.21 (dd, J=8.6 and 2.5 Hz, 1H), 4.07 (d, J=6.9 Hz, 1H), 2.09–2.03 (m, 1H), 1.37 (d, J=6.9 Hz, 6H), 1.00 (d, J=6.7 Hz, 6H); $^{13}$C NMR: δ 173.40, 168.24, 160.28, 155.91, 154.85, 134.28, 133.06, 131.12, 130.67, 126.45, 123.23, 73.97, 45.34, 27.64, 19.95, 18.91. MS m/z 442 (M$^+$), 386, 352, 341, 314, 248, 179, 156, 114.

N-(3,4-dichlorophenyl)-N'-(1-isopropyl-4,5-dioxoimidazolidin-2-ylidene)-N"-(tert-butoxycarbonyl)-guanidine (3c): To the mixture of N-(3,4-dichlorophenyl)-N'-(1-isopropyl-4,5-dioxoimidazolidin-2-ylidene)guanidine (3) (50 mg, 0.146 mmol) and DMF (5 ml) was added DMAP (1.8 mg), followed by di-tert-butyl dicarbonate (127 mg, 0.58 mmol), and the reaction mixture was further stirred at room temperature overnight. After being quenched with water, the mixture was extracted with CHCl$_3$, dried over Na$_2$SO$_4$, and concentrated. The crude product was purified by recrystallization from EtOAc/CHCl$_3$ to furnish 3c as a yellow needle (15.5 mg, 24%), mp 226° C. $^1$H NMR (600 MHz, CDCl$_3$): δ 7.81 (d, J=2.3 Hz, 1H), 7.50 (d, J=8.6 Hz, 1H), 7.23 (dd, J=8.6 and 2.3 Hz, 1H), 4.42 (m, 1H), 1.57 (s, 9H), 1.37 (d, J=7.0 Hz, 6H). $^{13}$C NMR: δ 156.32, 134.82, 133.51, 131.45, 131.03, 126.77, 126.68, 123.55, 86.72, 45.69, 28.42, 20.35. MS m/z: 442 (M$^+$), 390, 387, 331, 288, 248, 204.m N-(3,4-dichlorophenyl)-N'-(benzyloxycarbonyl)-N"-(1-isopropyl-4,5-dioxo-imidazolidin-2-ylidene)-guanidine (3d): Compound 3d was prepared by the same method for preparation of 3a, treating pure compound 3 with benzyl chloroformate to yield compound 3d as a pale yellow solid (63%), m.p. 235° C. $^1$H NMR (CDCl$_3$, 600Hz) δ 7.81 (1H, s), 7.53 (1H, d, J=8.6), 7.42–7.45 (5H, m), 7.23 (1H, d, J=8.6), 5.32 (2H, s), 4.43 (1H, m), 1.39 (6H, d). Anal. (C$_{21}$H$_{19}$N$_5$O$_4$Cl$_2$) C, H, N, Cl.

N-(3,4-dichlorophenyl)-N'-(1-hexyloxycarbonyl)-N"-(1-isopropyl-4,5-dioxo-imidazolidin-2-ylidene)-guanidine (3e): Compound 3e was prepared by the same method as 3a using hexyl chloroformate to yield compound 3d as a yellow crystals (0.6 g, 31%). $^1$H NMR (300 MHz, CDCl$_3$) δ 7.84 (d, J=2.5 Hz, 1H), 7.53 (d, J=8.6 Hz, 1H), 7.23 (dd, J=8.6 and 2.4 Hz, 1H), 4.49–4.40 (m, 1H), 4.31 (t, J=6.7 Hz, 2H), 1.82–1.72 (m, 3H), 1.58 (s, 5H), 1.40 (d, J=6.9 Hz, 6H), 0.94 (t, J=6.4 Hz, 3H); $^{13}$C δ 173.10, 168.10, 160.50, 155.89, 154.82, 134.27, 133.07, 131.30, 130.67, 126.44, 123.20, 68.29, 45.35, 31.31, 28.38, 25.31, 22.48, 19.95, 13.99. MS m/z 472, 470 (M$^+$), 416, 368, 316, 260, 186, 156. Anal. (C$_{20}$H$_{25}$Cl$_2$N$_5$O$_4$): C, H, N N-(3,4-dichloro-phenyl)-N'-(5-methyl-2-oxo-1,3-dioxol-4-yl)methyl-N"-(1-isopropyl-4,5-dioxo-imidazolidin-2-ylidene)guanidine (3f): A dimethylformamide suspension of compound 3 (200 mg, 0.58 mmol) was treated with (5-methyl-1,3-dioxolene-2-one-4-yl)-methyl p-nitrophenyl carbonate (204 mg, 0.69 mmol) and DMAP (14 mg, 0.11 mmol). See U.S. Pat. No. 5,466,811, which is herein incorporated by reference. The reaction mixture was stirred at room temperature overnight and partitioned in chloroform/H$_2$O. The water layer was extracted several times with chloroform. The organic layer was washed with brine, water, dried with Na$_2$SO$_4$, filtered and concentrated to yield crude product as yellow gum (258 mg). The crude product solidified upon treatment with ethyl acetate/hexane (1:1) to get yellow solid (91 mg, 31% yield), m.p. 144° C. $^1$H NMR (CDCl$_3$, 300 Hz): δ 7.73 (1H, d, J=2.4), 7.50 (d, J=8.6, 1H,), 7.20 (1H, dd, J=8.6, J=2.4), 5.01 (s, 2H), 4.41 (1H, m), 2.23 (s, 3H), 1.36 (d, J=6.9 Hz, 6H). MS (m/z) 497 (M$^+$). Anal. (C$_{19}$H$_{17}$N$_5$O$_7$Cl$_2$) C, H, N.

N-(3,4-dichlorophenyl)-N'-(3-butenyloxycarbonyl)-N"-(1-isopropyl-4,5-dioxoimidazolidin-2-ylidene)-guanidine (3g): Compound 3g was prepared by the same method for preparation of 3a, using pure compound 3 (100 mg) and butenyl chloroformate to yield compound 3g as a pale yellow solid (66 mg, 52%). $^1$H NMR (300 MHz, CDCl$_3$) δ 7.83 (d, J=2.5 Hz, 1H), 7.53 (d, J=8.6 Hz, 1H), 7.23 (dd, J=8.6 and 2.5 Hz, 1H), 5.89–5.78 (m, 1H), 5.24–5.16 (m, 2H), 4.49–4.42 (m, 1H), 4.40 (t, J=7.1 Hz, 2H), 2.54 (q, J=6.8 Hz, 2H), 1.40 (d, J=6.9 Hz, 6H); $^{13}$C NMR: δ 173.10, 168.10, 160.18, 155.95, 154.81, 134.27, 133.07, 132.57, 131.14, 130.68, 126.45, 123.22, 118.44, 66.90, 45.37, 32.78, 19.95. MS m/z 442, 440 (M$^+$), 351, 267, 191, 155. Anal. (C$_{18}$H$_{19}$Cl$_2$N$_5$O$_4$): C, H, N.

N-(3,4-dichloro-phenyl)-N'-(2-benzyloxyethoxycarbonyl)-N"-(1-isopropyl-4,5-dioxo-imidazolidin-2-ylidene)-guanidine (3h): Compound 3h was prepared by the same method as that of 3a, using pure compound 3 and benzyloxyethyl chlorformate, to yield compound 3h as a white crystal (0.4 g, 22%). $^1$H NMR (300 MHz, CDCl$_3$) δ 13.17 (s, 1H), 11.08 (s, 1H), 7.81 (d, J=2.4 Hz, 1H), 7.51 (d, J=8.6 Hz, 1H), 7.39–7.29 (m, 5H), 7.21 (dd, J=8.6 and 2.4 Hz, 1H, 4.61 (s, 2H), 4.49–4.42 (m, 3H), 3.78 (t, J=4.7 Hz, 2H), 1.39 (d, J=6.9 Hz, 6H); $^{13}$C δ 172.50, 167.60, 160.10, 150.04, 155.30, 155.00, 138.00, 137.47, 134.31, 133.04, 131.21, 130.66, 128.54, 128.48, 127.94, 127.85, 127.80, 126.47, 123.25, 73.30, 71.35, 67.16, 66.66, 64.56, 61.92, 45.40, 19.94, MS m/z 522, 520 (M$^+$),492, 432, 370, 368, 298, 232, 181. Anal. (C$_{24}$H$_{25}$Cl$_2$N$_5$O$_5$): C, H, N.

N-[1-(3,4-dichlorophenyl)-4,5-dioxo-4,5-dihydro-1H-imidazol-2-yl]-N'-isopropylguanidine (4): 1-(3,4-dichlorophenyl)-2-methylsulfanyl-1H-imidazole-4,5-dione (15, 1.89 g, 6.54 mmol) was dissolved in 10 ml of dried DMF and cooled with an ice bath to 0° C. To the solution was added dropwise 40 ml of DMF solution containing guanidine 18 (1.369 g, 13.554 mmol). The solution was stirred at room temperature for 2 hours after addition and then further stirred at 50° C. for 24 hours. The solvent DMF was dried under vacuum and the crude product was suspended in 30 ml of chloroform. The yellow solid was collected, washed sequentially with 3×20 ml of CHCl$_3$ and 10 ml of methanol to afford compound 4 as a white color powder (1.588 g, 6.54 mmol, 71%), mp 245° C.: NMR indicates that the compound exists in two tautomeric forms in the CDCl$_3$ solution. $^1$H NMR (600 MHz, DMSO-d6) (Major tautomer): δ 8.74–8.69 (m, 1H), 7.79 (d, J=8.6 Hz, 1H), 7.76 (d, J=2.2 Hz, 1H), 7.44 (dd, J=8.6 and 2.2 Hz), 3.73 (m, 1H), 1.14 (d, J=6.4 Hz, 6H); $^{13}$C NMR: δ 168.60, 162.45, 161.15, 161.09, 134.01, 131.84, 131.48, 131.20, 130.29, 128.86. IR: 1757, 1722, 1645, 1595, 1551, 1535, 1480, 1304, 997, 754 cm$^{-1}$; MS (m/z): 342 (M$^+$), 271, 229, 187, 127. Anal. (C$_{13}$H13Cl$_2$N$_5$O$_2$.0.25H$_2$O) C, H, Cl, N.

Minor tautomer: $^1$H NMR. $^1$H NMR (600 MHz, DMSO-d6) δ 8.35 (s), 7.99 (s), 7.88 (d, J=7.3 Hz), 7.42 (dd, J=8.6 and 2.2 Hz), 1.14 (d, J=6.4 Hz).

Compound 4 was also prepared by an alternate method: A solution of 4c (0.424 g, 0.959 mmol) in dry CHCl$_3$ (60 ml) was cooled with an ice-bath. To the solution was added dropwise of concentrated HCl (2 ml), stirred at 0° C. for an hour and then at room temperature overnight. Saturated Na$_2$CO$_3$ was added to basicify the mixture. The white solid was collected, washed successively with CHCl$_3$ and water and dried under reduced pressure to afford 4 as a white solid (0.292 g, 0.854 mmol, 89%), mp 244° C. Both NMR spectrum of compound 4 made by the two methods are identical.

N-[-(3,4-dichlorophenyl)-4,5-dioxo-imidazolidin-2-ylidene]-N'-isopropyl-N"-(ethylcarbonyl)guanidine (4a): Compound 4a was prepared by two methods. Method A: Followed the same procedure for the preparation of 3a, using pure compound 4 (0.788 g, 2.304 mmol), instead of compound 3, as starting material to yield compound 4a as a white solid (0.632 g, 66%), m.p. 257° C. $^1$H NMR (CDCl$_3$, 600 Hz) δ 7.56 (d, J=2.4 Hz, 1H), 7.55 (d, J=8.3 Hz, 1H), 7.29 (dd, J=2.4 Hz, J=8.3 Hz, 1H), 4.32 (q, J=7.1 Hz, 2H), 4.16 (m, 1H), 1.39 (t, J=7.1 Hz, 3H), 1.25 (d, J=6.6 Hz, 6H). Anal. (C$_{16}$H$_{17}$N$_5$O$_4$Cl$_2$) C, H, N.

Method B: Adapted the alternative method for the preparation of 4d as follows: To the solution of the crude dione 15 (0.413 g, 1.429 mmol) in 50 ml of dry CHCl$_3$ was added N-isopropyl-N'-(ethylcarbonyl)guanidine (0.206 g, 1.191 mmol). The reaction mixture was heated at 50° C. for 48 hours. The reaction was quenched with water, extracted with chloroform and dried over Na$_2$SO$_4$. The solvent was removed in vacuo and the crude product was purified with a silica gel column using 3% EtOAc/CHCl$_3$ as eluent to yield 4a as a white solid (0.115 g, 20%).

The melting point and NMR of compound 4a made by both procedures are identical.

N-[1-(3,4-dichlorophenyl)-4,5-dioxo-imidazolidin-2-ylidene]-N'-isopropyl-N"-(isobutyloxycarbonyl)guanidine (4b): Method A: WR182393 (a crude mixture, 5 g) was suspended in 100 ml of CHCl$_3$. To the suspension was added 9.17 ml of dry triethyl amine and the mixture was stirred at room temperature for 30 minutes. On cooling with an ice bath, isobutyl chloroformate (7.95 ml) was added drop-wise to the suspension. The ice bath was removed after the addition finished, and the reaction mixture was further stirred at room temperature for 2 hours. The clear CHCl$_3$ solution was washed with H$_2$O three times, dried over Na$_2$SO$_4$ and evaporated under reduced pressure to small volume. The crude product was collected and recrystallized (EtOAc/CHCl$_3$, 1:10 v/v) to afford the pure isobutyl carbamate derivative as white needles (1.979 g, 31% yield), mp 260° C. $^1$H NMR (600 MHz, CDCl$_3$): δ12.44(s, 1H), 9.24 (d, J=7.2 Hz, 1H), 7.55 (d, J=2.4 Hz, 1H), 7.54 (d, J=8.6 Hz, 1H), 7.28(dd, J=8.6 and 2.4 Hz, 1H), 4.12 (m, 1H), 4.02 (d, J=6.6 Hz, 2H), 2.05 (m, 1H), 1.24 (d, J=6.6 Hz, 6H), 0.99 (d, J=6.7 Hz, 6H); $^{13}$C NMR: δ 170.73, 168.08, 159.18, 155.88, 154.10, 132.49, 132.10, 131.26, 130.35, 128.58, 125.6173.91, 45.15, 27.57, 22.20, 18.84. IR: 1769, 1723, 1624, 1546, 1472, 1387, 1308, 1242, 1205, 1059, 754 cm$^{-1}$. MS (m/z): 442 (M$^+$), 376, 316, 314, 272, 202. Anal. (C$_{18}$H$_{21}$Cl$_2$N$_5$O$_4$): C, H, N, Cl.

Method B: Compound 4b was also prepared by the same procedure as method A, except, pure compound 4 (25 mg), instead of the mixture WR182393, was used as starting material to yield compound 4b as a white crystals (15 mg, 47%). The NMR and the melting point of compound 4b made by both methods are identical.

N-[1-(3,4-dichlorophenyl)-4,5-dioxo-imidazolidin-2-ylidene]-N'-isopropyl-N"-(tert-butoxycarbonyl)guanidine (4c): To the solution of the crude dione 15 (0.7 g, 2.5 mmol) in 25 ml of dry CHCl$_3$ was added N-isopropyl-N'-(tert-butoxycarbonyl)-guanidine (17) (0.5 g, 2.5 mmol). The reaction mixture was heated at 50° C. for 16 hours. The reaction was quenched with water, extracted with chloroform and dried over Na$_2$SO$_4$. The solvent was removed in vacuo and the crude product was purified with a silica gel column and was eluted with 3% EtOAc/CHCl$_3$ to yield 4c as a white solid (0.25 g, 22%), mp 227° C. $^1$H NMR (300 MHz, CDCl$_3$): δ 7.55 (d, J=2.4 Hz, 1H), 7.53(d, J=8.6 Hz, 1H), 7.27 (dd, J=8.6 and 2.4 Hz, 1H), 4.15 (m, 1H), 1.54 (s, 9H), 1.24 (d, J=6.6 Hz, 6H); $^{13}$C NMR: δ 170.50, 168.40, 159.34, 156.09, 153.00, 132.51, 132.09, 131.34, 130.38, 128.62, 125.62, 85.59, 45.05, 29.70, 22.34. IR: 2979, 2930, 1766, 1729, 1532, 1474, 1142, 775, 734 cm$^{-1}$. MS (m/z): 444 (M$^+$+1).

The alternative method also have been successfully achieved by the following procedure: To the suspension of N-[1-(3,4-dichlorophenyl)-4,5-dioxo-4,5-dihydro-1H-imidazol-2-yl]-N'-isopropylguanidine (4) (27 mg, 0.079 mmol) in CHCl$_3$ (5 ml) was added first solid DMAP (0.964 mg, 0.0079 mmol), followed by addition of di-tert-butyldicarbonate (19 mg, 0.087 mmol)/CHCl$_3$ solution (10 ml) and the reaction mixture was stirred at room temperature overnight. The reaction was quenched with water, extracted with CHCl$_3$ three times. The chloroform extracts were combined, dried over Na$_2$SO$_4$, and concentrated. The residue was purified by flash silica gel column chromatography and eluted with 10 to 30% diethyl ether in hexanes to furnish 4c as crystals (11 mg, 31%). The NMR spectrum of the compound prepared by the alternate method is identical to the sample prepared by the condensation of compound 15 and 17.

N-[1-(3,4-dichlorophenyl)-4,5-dioxo-imidazolidin-2-ylidene]-N'-isopropyl-N"-(benzyloxycarbonyl)guanidine (4d): To the solution of the crude dione 15 (0.10 g, 0.346 mmol) in 25 ml of dry CHCl$_3$ was added N-(benzyloxycarbonyl)-N'-isopropylguanidine (16) (0.122 g, 0.519 mmol) at room temperature. The reaction mixture was heated at 50° C. for 18 hours and then quenched with water. The mixture was extracted with chloroform and dried over Na$_2$SO$_4$. The CHCl$_3$ was removed in vacuo and the crude product was recrystallized from hexanes/CHCl$_3$ to yield compound 4d as light yellow crystals (51 mg, 0.11 mmol, 31%), mp 211° C. $^1$H NMR (300 MHz, CDCl$_3$): δ 7.54–7.51(m, 2H), 7.41 (s, 5H), 7.25 (dd, J=8.6 and 2.4 Hz, 1H), 5.25 (s, 2H), 4.12 (m, 1H), 2.46 (d, J=6.6 Hz, 6H). $^{13}$C NMR: δ 170.83, 155.86, 153.87, 133.89, 132.56, 132.19, 131.22, 130.42, 129.21, 128.93, 128.65, 128.61, 125.60, 69.24, 45.25, 22.28. MS (m/z): 476 (M$^+$), 370, 316, 314, 236. Anal. (C$_{21}$H$_{19}$Cl$_2$N$_5$O$_4$) C, H, Cl, N.

N-[1-(3,4-dichlorophenyl)-4,5-dioxo-imidazolidin-2-ylidene]-N'-isopropyl-N"-(1-hexyloxycarbonyl)guanidine (4e): Compound 4e was prepared by the same method for preparation of 4b, using pure compound 4 (0.800 g, 2.34 mmol) and hexyl chloroformate as starting materials to yield compound 4e as a white color crystal (0.354 g, 32%). $^1$H NMR (300 MHz, CDCl$_3$) δ 12.45 (s, 1H), 7.57–7.54 (m, 2H), 7.31–7.27 (dd, J=8.5 and 2.4 Hz, 1H), 4.25 (t, J=6.8 Hz, 2H), 4.12 (m, 1H),1.74 (m, 2H), 1.35 (m, 6H), 1.25 (d, J=6.6 Hz, 6H), 0.93 (t, J=6.4 Hz, 3H); $^{13}$C NMR: δ170.78, 168.50, 159.20, 155.93, 154.15, 132.56, 132.18, 131.50, 130.41, 128.62, 125.61, 31.31, 28.38, 25.32, 22.49, 22.30, 14.00. MS m/z 470 (M$^+$), 418, 416, 368, 342, 314, 272, 230, 174.

N-[1-(3,4-dichlorophenyl)-4,5-dioxo-imidazolidin-2-ylidene]-N'-isopropyl-N"-(3-butenyloxycarbonyl)guanidine (4g): Compound 4g was prepared by the same method for preparation of 4b, using pure compound 4 (0.200 g, 585 mmol) and butenyl chloroformate as starting materials to yield compound 4g as a white color solid (98 mg, 38%). $^1$H NMR (300 MHz, CDCl$_3$) δ 12.46 (s, 1H), 9.22 (s, 1H), 7.56–7.53 (m, 2H), 7.30–7.26 (dd, J=8.6 and 2.4 Hz, 1H), 5.85–5.72 (m, 1H), 5.20–5.13 (m, 2H), 4.29 (t, J=6.9 Hz, 2H), 4.16 (m, 1H), 2.47 (q, J=6.8 Hz, 2H), 1.24 (d, J=6.6 Hz, 6H); $^{13}$C NMR: δ170.76, 168.08, 159.19, 155.88, 153.96, 132.63, 132.53, 131.26, 130.40, 128.61, 125.65, 118.32, 66.60, 45.23, 32.74, 22.27; MS m/z 440 (M$^+$), 388, 338, 269, 245, 180, 159.

Assessment of Antimalarial Activity in Rhesus Monkeys

The causal prophylactic antimalarial activity of the two 2-guanidinylimidazolidinedione carbamates 3c and 4b were assessed against *Plasmodium cynomolgi* in Rhesus monkey. Two monkeys were used in each test group. The average control animal developed parasitemia is about 10 days after inoculation of about 1×10$^6$ *P. cynomolgi* sporozoites harvested from *Anopheles dirus*. The results are shown in the following Table 1:

TABLE 1

Causal Prophylactic Activity

| Monkey No. | Group | Drug | Day of Parasitemia | Results* |
|---|---|---|---|---|
| DA889 | Control | None | Parasitemia on day 10 | Valid control |
| DA891 | | (DMSO) | Parasitemia on day 13 | Valid control |
| DA888 | 1 | WR182393, 30 mg/kg | Parasitemia on day 75 | Delay the parasitemia |
| DA895 | | | Parasite free on day 100 | Causal prophylaxis |
| DA874 | 2 | 4b, 30 mg/kg | Parasite free on day 100 | Causal prophylaxis |
| DA894 | | | | |
| DA880 | 3 | 4b, 10 mg/kg | Parasitemia on day 47 | Delay the parasitemia |
| DA883 | | | Parasite free on day 100 | Causal prophylaxis |
| DA873 | 4 | 3c, 30 mg/kg | Parasite free on day 100 | Causal prophylaxis |
| DA877 | | | | |
| DA875 | 5 | 3c, 10 mg/kg | | |
| DA878 | | | | |

*Treated monkeys remained parasite free for 100 days after the treatment were considered causal prophylaxis or protected.

The positive control drug, WR182393, at 30 mg/kg given i.m., protected one monkey and delayed parasitemia in the other monkey for 62 days, confirming the previously report that this compound possessed i.m. causal prophylactic and radical curative activity against *P. cynomologi*. See Corcoran, K D, et al. (1993) Am. J. Trop. Med. Hyg. 49:473–477, which is herein incorporated by reference. Both monkeys that received 30 mg/kg of compound 4b were protected and stayed parasite free 100 days after treatment. At lower dose of 10 mg/kg, one monkey remained parasite free after day 100, but the other monkey developed parasitemia after day 47. However, compound 3c showed the best prophylactic efficacy among the three compounds tested. It protected all four monkeys received either 10 mg/kg or 30 mg/kg dosages. Nevertheless, all three compounds studied showed no to minimum protective activity up to 30 mg/kg administered orally. Treated monkeys remained parasite free for 100 days after the treatment were considered cured or protected.

Therefore, the present invention provides novel synthetic and purification methods for making and purifying 2-guanidinylimidazolidinedione compounds. As used herein, the phrase "2-guanidinylimidazolidinedione compounds" refers to compounds having the following structural formulas A or B:

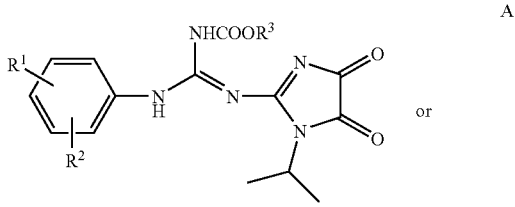

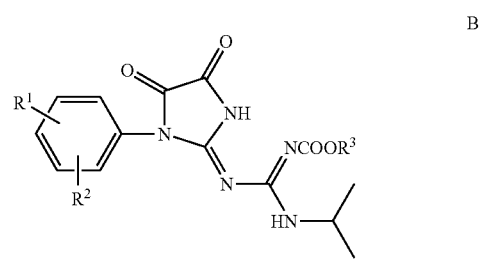

wherein R$^1$ and R$^2$ are each independently a hydrogen, halogen, alkyl, amino, alkylamino or alkoxyl which may be substituted or unsubstituted; and wherein R$^a$ is an alkyl, cycloalkyl, heterocycloalkyl, acyl, aryl, heteroaryl, alkylaryl, sulfonyl, or alkylsulfonyl. In some preferred embodiments, R$^1$ and R$^2$ are each independently —H, —Cl, —Br, —CF$_3$, —OCH$_3$, or —OCF$_3$. In some preferred embodiments, R$^3$ is —CH$_2$CH$_3$, —CH$_2$CH(CH$_3$)$_2$, —C(CH$_3$)$_3$, —CH$_2$C$_6$H$_5$, —(CH$_2$)$_5$CH$_3$,

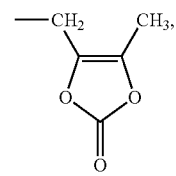

—CH$_2$CH$_2$C═CH$_2$, or —CH$_2$CH$_2$OCH$_2$C$_6$H$_5$.

2-Guanidinylimidazolidinedione compounds also include those provided in the following Tables 2 and 3:

TABLE 2

![Structure with NHCOOR^a group, dichlorophenyl, and imidazolidinedione with isopropyl]

| Compound | R$^a$ |
|---|---|
| 3a | —CH$_2$CH$_3$ |
| 3b | —CH$_2$CH(CH$_3$)$_2$ |
| 3c | —C(CH$_3$)$_3$ |
| 3d | —CH$_2$C$_6$H$_5$ |
| 3e | —(CH$_2$)$_5$CH$_3$ |
| 3f | —CH$_2$-(4-methyl-1,3-dioxol-2-one-5-yl) |
| 3g | —CH$_2$CH$_2$C=CH$_2$ |
| 3h | —CH$_2$CH$_2$OCH$_2$C$_6$H$_5$ |

TABLE 3

![Structure with dichlorophenyl on imidazolidinedione, NCOOR^8 and HN-isopropyl guanidine]

| Compound | R$^a$ |
|---|---|
| 4a | —CH$_2$CH$_3$ |
| 4b | —CH$_2$CH(CH$_3$)$_2$ |
| 4c | —C(CH$_3$)$_3$ |
| 4d | —CH$_2$C$_6$H$_5$ |
| 4e | —(CH$_2$)$_5$CH$_3$ |
| 4g | —CH$_2$CH$_2$C=CH$_2$ |

The 2-guanidinylimidazolidinedione compounds of the present invention have valuable pharmaceutical properties. In particular, the 2-guanidinylimidazolidinedione compounds, as provided herein exhibit excellent activity against malaria pathogens as provided in the Examples. Therefore, the present invention provides methods of preventing, treating, or inhibiting malaria in a subject which comprises administering to the subject at least one 2-guanidinylimidazolidinedione compound of the present invention.

In some embodiments, the present invention provides 2-guanidinylimidazolidinedione compounds that exhibit prophylactic antimalarial activity. Thus, the present invention provides methods of treating, preventing, or inhibiting diseases and disorders associated with malaria which comprises administering at least one 2-guanidinylimidazolidinedione compound of the present invention. Diseases and disorders associated with malaria include those caused by a *Plasmodium* parasite such as *Plasmodium falciparum*, *Plasmodium vivax*, *Plasmodium ovale*, and the like.

In accordance with a convention used in the art,

is used in structural formulas and "—" as in, for example, "—CH$_3$" herein to depict the bond that is the point of attachment of the moiety or substituent to the core or backbone structure.

Where chiral carbons are included in chemical structures, unless a particular orientation is depicted, both sterioisomeric forms are intended to be encompassed.

An "alkyl" is intended to mean a straight or branched chain monovalent radical of saturated and/or unsaturated carbon atoms and hydrogen atoms, such as methyl (Me), ethyl (Et), propyl (Pr), isopropyl (i-Pr), butyl (n-Bu), isobutyl (i-Bu), t-butyl (t-Bu), (sec-Bu), ethenyl, pentenyl, butenyl, propenyl, ethynyl, butynyl, propynyl, pentynyl, hexynyl, and the like, which may be unsubstituted (i.e., contain only carbon and hydrogen) or substituted by one or more suitable sustituents as defined below (e.g., one or more halogen, such as F, Cl, Br, or I, with F and Cl being preferred). A "lower alkyl group" is intended to mean an alkyl group having from 1 to 8 carbon atoms in its chain.

A "cycloalkyl" is intended to mean a non-aromatic monovalent monocyclic, bicyclic, or tricyclic radical comprising 3–14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents. Illustrative examples of cycloalkyl groups include the following moieties:

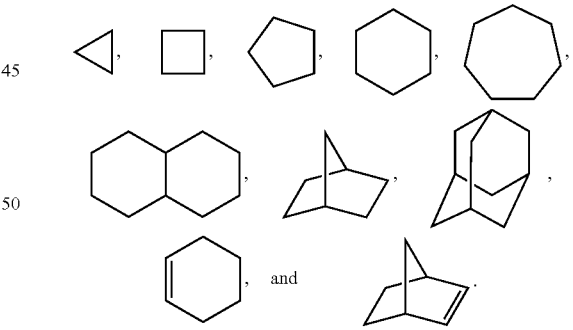

A "heterocycloalkyl" is intended to mean a non-aromatic monovalent monocyclic, bicyclic, or tricyclic radical, which is saturated or unsaturated, comprising 3–18 ring members, which includes 1–5 heteroatoms selected from nitrogen, oxygen, and sulfur, where the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include the following moieties:

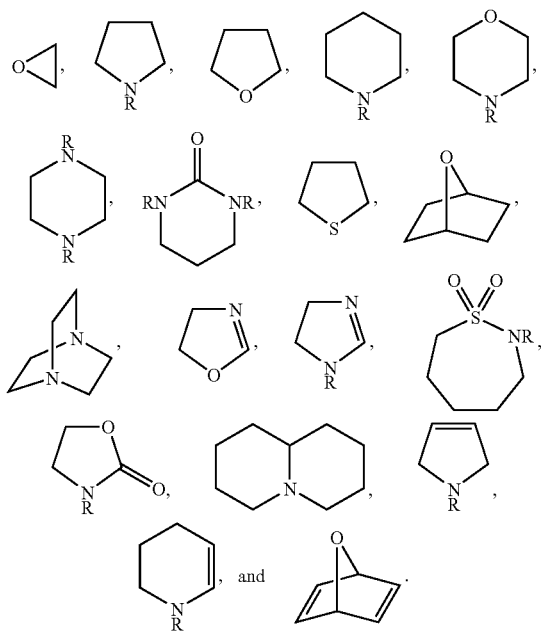

An "aryl" is intended to mean an aromatic monovalent monocyclic, bicyclic, or tricyclic radical comprising 6, 10, 14, or 18 carbon ring members, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Illustrative examples of aryl groups include the following moieties:

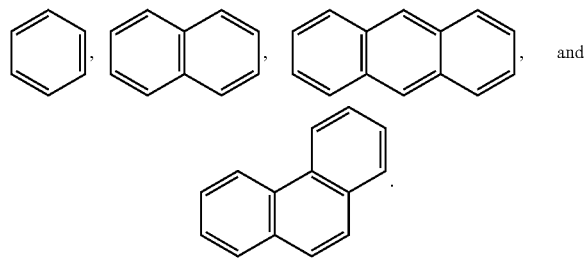

A "heteroaryl" is intended to mean an aromatic monovalent monocyclic, bicyclic, or tricyclic radical comprising 4–18 ring members, including 1–5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include the following moieties:

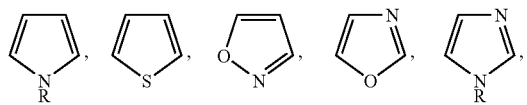

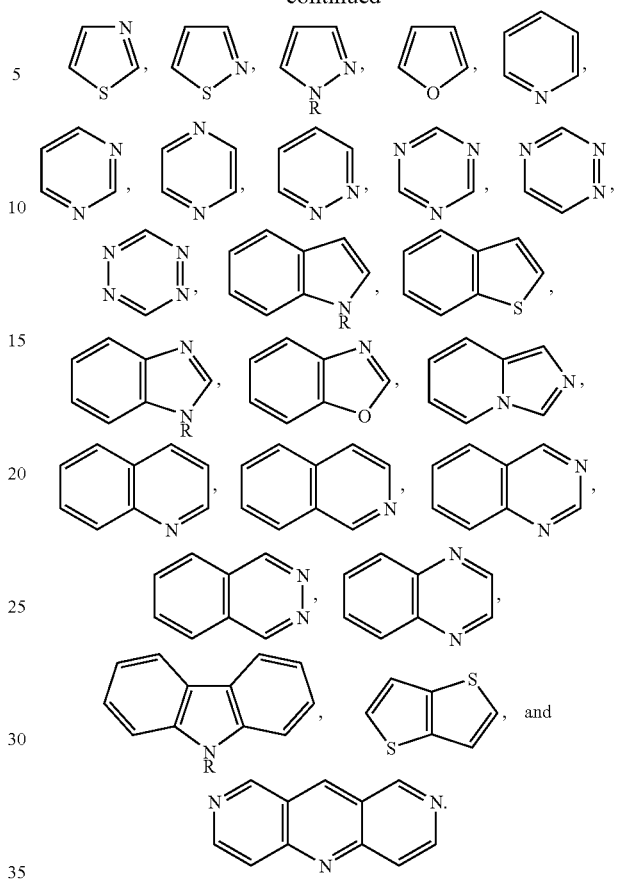

A "heterocycle" is intended to mean a heteroaryl or heterocycloalkyl group (each of which, as defined above, are optionally substituted).

The terms "aryl" (Ar) and "heteroaryl" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like.

An "acyl" is intended to mean a —C(O)—$R^a$ radical, where $R^a$ is a suitable substituent as defined below.

A "thioacyl" is intended to mean a —C(S)—$R^a$ radical, where $R^a$ is a suitable substituent as defined below.

A "sulfonyl" is intended to mean a —SO$_2$$R^a$ radical, where $R^a$ is a suitable substituent as defined below.

A "hydroxyl" is intended to mean the radical —OH.

An "amino" is intended to mean the radical —NH$_2$.

An "alkylamino" is intended to mean the radical —NH$R^a$, where $R^a$ is an alkyl group.

A "dialkylamino" is intended to mean the radical —N$R^a$$R^b$, where $R^a$ and $R^b$ are each independently an alkyl group.

An "alkoxyl" is intended to mean the radical —O$R^a$, where $R^a$ is an alkyl group. Exemplary alkoxyl groups include methoxyl, ethoxyl, propoxyl, and the like.

An "alkoxycarbonyl" is intended to mean the radical —C(O)OR$^a$, where R$^a$ is an alkyl group.

An "alkylsulfonyl" is intended to mean the radical —SO$_2$R$^a$, where R$^a$ is an alkyl group.

An "alkylaminocarbonyl" is intended to mean the radical —C(O)NHR$^a$, where R$^a$ is an alkyl group.

A "dialkylaminocarbonyl" is intended to mean the radical —C(O)NR$^a$R$^b$, where R$^a$ and R$^b$ are each independently an alkyl group.

A "mercapto" is intended to mean the radical —SH.

An "alkylthio" is intended to mean the radical —SR$^a$, where R$^a$ is an alkyl group.

A "carboxyl" is intended to mean the radical —C(O)OH.

A "carbamoyl" is intended to mean the radical —C(O)NH$_2$.

An "aryloxyl" is intended to mean the radical —OR$^c$, where R$^c$ is an aryl group.

A "heteroaryloxyl" is intended to mean the radical —OR$^d$, where R$^d$ is a heteroaryl group.

An "arylthio" is intended to mean the radical —SR$^c$, where R$^c$ is an aryl group.

A "heteroarylthio" is intended to mean the radical —SR$^d$, where R$^d$ is a heteroaryl group.

A "leaving group" (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

A "protecting group" is intended to refer to groups that protect one or more inherent functional group from premature reaction. Suitable protecting groups may be routinely selected by those skilled in the art in light of the functionality and particular chemistry used to construct the compound. Examples of suitable protecting groups are described, for example, in Greene and Wuts, Protective Groups in Organic Synthesis, 3$^{rd}$ edition, John Wiley and Sons, New York, New York (1999).

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxyl groups, carboxyl groups, amino groups, alkylamino groups, dialkylamino groups, carbamoyl groups, arylthio groups, heteroarylthio groups, and the like.

In general, the various moieties or functional groups for variables in the formulae may be "optionally substituted" by one or more suitable "substituents". The term "substituent" or "suitable substituent" is intended to mean any suitable substituent that may be recognized or selected, such as through routine testing, by those skilled in the art. Illustrative examples of useful substituents are those found in the exemplary compounds that follow, as well as halogen (chloro, iodo, bromo, or fluoro); $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O. All of these substituents may optionally be further substituted with a substituent selected from groups such as hydroxyl groups, halogens, oxo groups, alkyl groups, acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, alkylamino groups, dialkylamino groups, carbamoyl groups, aryloxyl groups, heteroaryloxyl groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

It is understood that while a compound of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Some of the compounds of the present invention may exist as single stereoisomers (i.e., essentially free of other stereoisomers), racemates, or mixtures of enantiomers, diastereomers, or both. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, if the compounds of the present invention are made synthetically, they are used in a form that is at least 90% optically pure, that is, a form that comprises at least 90% of a single isomer (80% enantiomeric excess (e.e.) or diastereomeric excess (d.e.), more preferably at least 95% (90% e.e. or d.e.), even more preferably at least 97.5% (95% e.e. or d.e.), and most preferably at least 99% (98% e.e. or d.e.).

Additionally, the structural formulas herein are intended to cover, where applicable, solvated as well as unsolvated forms of the compounds. A "solvate" is intended to mean a pharmaceutically acceptable solvate form of a specified compound that retains the biological effectiveness of such compound. Examples of solvates include compounds of the invention in combination with water, isopropanol, ethanol, methanol, dimethyl sulfoxide, ethyl acetate, acetic acid, ethanolamine, or acetone. Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulas include compounds having the indicated structure, including the hydrated as well as the non-hydrated forms.

As indicated above, the compounds of the invention also include active tautomeric and stereoisomeric forms of the compounds of the present invention, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

Additionally, the compounds of the invention include pharmaceutically acceptable salts, multimeric forms, prodrugs, active metabolites, precursors and salts of such metabolites of the compounds of the present invention.

The term "pharmaceutically acceptable salts" refers to salt forms that are pharmacologically acceptable and substantially non-toxic to the subject being treated with the compound of the invention. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

The term "multimer" refers to multivalent or multimeric forms of active forms of the compounds of the invention. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to receptor binding. Provision of such multivalent forms of active receptor-binding compounds with optimal spacing between the receptor-binding moieties may enhance receptor binding. See, for example, Lee et al., (1984) Biochem. 23:4255. The artisan may control the multivalency and spacing by selection of a suitable carrier moiety or linker units. Useful moieties include molecular supports comprising a multiplicity of functional groups that can be reacted with functional groups associated with the active compounds of the invention. A variety of carrier moieties may be used to build highly active multimers, including proteins such as BSA (bovine serum albumin) or peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound. "A pharmaceutically active metabolite" is intended to mean a pharmacologically active product produced through metabolism in the body of a specified compound or salt thereof. Prodrugs and active metabolites of a compound may be identified using routine techniques known in the art See, e.g., Bertolini, G. et al., (1997) J. Med. Chem. 40:2011–2016; Shan, D. et al., J. Pharm. Sci., 86(7):765–767; Bagshawe K., (1995) Drug Dev. Res. 34:220–230; Bodor, N., (1984) Advances in Drug Res. 13:224–331; Bundgaard, H., *Design of Prodrugs* (Elsevier Press, 1985); and Larsen, I. K., *Design and Application of Prodrugs*, Drug Design and Development (Krogsgaard-Larsen et al., eds., Harwood Academic Publishers, 1991).

If the compound of the present invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrvic acid, oxalic acid, glycolic acid, salicylic acid, a pyranosidyl acid, such as glucuronic acid or galacturonic acid, an α-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the present invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from basic amino acids, such as lysine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of compounds that are solids, it is understood by those skilled in the art that the compound of the present invention and salts may exist in different crystal or polymorphic forms, all of which are intended to be within the scope of the present invention and specified structural formulas.

The compounds of the present invention in accordance with the present invention are useful in the treatment malaria and diseases and disorders associated with malaria or a *Plasmodium* parasite.

The antimalarial of the compounds of the present invention may be measured by any of the methods available to those skilled in the art, including in vitro and in vivo assays. Examples of suitable assays for activity measurements are provided herein. Properties of the compounds of the present invention may be assessed, for example, by using one or more of the assays set out in the Examples below. Other pharmacological methods may also be used to determine the efficacy of the compounds as antimalarial agents.

The compounds of the present invention may be used in combination with or as a substitution for treatments of the above conditions. For example, the compounds of the present invention may also be used alone or combination with antimalarial agents known in the art. The compounds of the present invention may be used alone or in combination with supplementary active compounds including antibiotics, antiprotozoal agents, antifungal agents, and antiproliferative agents, and analgesics known in the art.

The specification for the dosage unit forms of the invention are dictated by and directly dependent on the unique characteristics of the active compound and the particular therapeutic effect to be achieved, and the limitations inherent in the art of compounding such an active compound for the treatment of individuals.

A compound of the present invention may be administered in a therapeutically effective amount to a mammal such as a human. Therapeutically effective amounts of the compounds of the present invention may be used to treat, modulate, attenuate, reverse, or affect malaria in a mammal. An "effective amount" is intended to mean that amount of an agent that is sufficient to treat, prevent, or inhibit malaria or a disease or disorder associated with malaria. In some preferred embodiments, malaria or the disease or disorder associated with malaria is caused by a *Plasmodium* parasite, preferably, *P. falciparum, P. vivax, P. ovale*, or *P. malariae*.

Thus, e.g., a "therapeutically effective amount" of a compound of the present invention, a prodrug, an active metabolite, or a salt thereof, is a quantity sufficient to, when administered to a mammal, treat, prevent, or inhibit malaria or a disease or disorder associated with malaria or a *Plasmodium* parasite. The amount of a given compound of the present invention that will correspond to such an amount will vary depending upon factors such as the given drug or compound, the pharmaceutical formulation and route of administration, the type of disease or disorder, the identity of the subject or host being treated, and the like, but can nevertheless be routinely determined by one skilled in the art. Also, as used herein, a "therapeutically effective amount" of a compound of the present invention is an amount which prevents, inhibits, suppresses, or reduces malaria (as determined by clinical symptoms or the amount of *Plasmodium* organisms) in a subject as compared to a control. As defined herein, a therapeutically effective amount of a compound of the present invention may be readily determined by one of ordinary skill by routine methods known in the art.

For example, a therapeutically effective amount of a compound of the invention ranges from about 0.1 to about 1,000 mg/kg body weight, preferably about 0.1 to about 500 mg/kg body weight, and more preferably about 0.1 to about 100 mg/kg body weight. The skilled artisan will appreciate that certain factors may influence the dosage required to effectively treat a subject, including but not limited to the severity of the disease or disorder, previous treatments, the general health and/or age of the subject, and other diseases present.

Preferred topical concentrations include about 0.1% to about 10% of at least one compound of the present invention in a formulated salve. The skilled artisan will appreciate that certain factors may influence the dosage required to effectively treat a subject, including but not limited to the severity of the disease or disorder, previous treatments, the general health and/or age of the subject, and other diseases present.

Moreover, treatment of a subject with a therapeutically effective amount of the compound of the present invention may consist of a single administration, or alternatively comprise a series of applications. For example, a subject may be treated with a compound of the present invention at least once. However, the subject may treated with the compound from about one time per week to about once daily for a given treatment period. The length of the treatment period will depend on a variety of factors such as the severity of inflammation, the concentration and activity of the compounds of the present invention, or a combination thereof. It will also be appreciated that the effective dosage of the compound used for treatment may increase or decrease over the course of a particular treatment. Changes in dosage may result and become apparent by standard diagnostic assays known in the art. In some instances chronic administration may be required. The compounds of the present invention may be administered before, during, after, or a combination thereof exposure to malaria or a *Plasmodium* parasite.

The pharmaceutical formulations of the invention comprise at least one compound of the present invention and may be prepared in a unit-dosage form appropriate for the desired mode of administration. The pharmaceutical formulations of the present invention may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the condition to be treated, and the chosen compound of the present invention.

It will be appreciated that the actual dosages of the compounds used in the pharmaceutical formulations of this invention will vary according to the particular complex being used, the particular composition formulated, the mode of administration, and the particular site, host, and disease being treated. Optimal dosages for a given set of conditions may be ascertained by those skilled in the art using conventional dosage determination tests in view of the experimental data for a given compound. Administration of prodrugs may be dosed at weight levels that are chemically equivalent to the weight levels of the fully active forms.

The compounds of the present invention can be incorporated into pharmaceutical formulations suitable for administration. Pharmaceutical formulations of this invention comprise a therapeutically effective amount of at least one compound of the present invention, and an inert, pharmaceutically or cosmetically acceptable carrier or diluent. As used herein the language "pharmaceutically or cosmetically acceptable carrier" is intended to include any and all solvents, dispersion media, coatings, antibacterial and antifungal agents, isotonic and absorption delaying agents, and the like, compatible with pharmaceutical or cosmetic administration. The pharmaceutical or cosmetic carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like. The use of such media and agents for pharmaceutically or cosmetically active substances is well known in the art.

Except insofar as any conventional media or agent is incompatible with the active compound, use thereof in the formulation is contemplated. Supplementary active compounds can also be incorporated into the formulations. Supplementary active compounds include antimalarials, antiproliferative agents, antibacterials, antiprotozoal agents, antifungal agents, anti-inflammatory agents, and other compounds commonly used to treat diseases and disorders related to cell proliferation, inflammation, and bacterial, protozoal, and fungal infections. Supplementary active compounds include:

Antimalarials such as chloroquine, quinine, mefloquine, amodiaquin, primaquine, pyrimethamine, sulfonamides, sulfones, dihydrofolate reductase inhibitors, tetrandine, derivatives thereof, and the like. As used herein, the term "antimalarial" refers to compounds that show activity against *Plasmodium* parasites using assays known in the art.

Antibiotics such as penicillin, cloxacillin, dicloxacillin, methicillin, nafcillin, oxacillin, ampicillin, amoxicillin, bacampicillin, azlocillin, carbenicillin, mezlocillin, piperacillin, ticarcillin, azithromycin, clarithromycin, clindamycin, erythromycin, lincomycin, demeclocycline, doxycycline, minocycline, oxytetracycline, tetracycline, quinolone, cinoxacin, nalidixic acid, fluoroquinolone, ciprofloxacin, enoxacin, grepafloxacin, levofloxacin, lomefloxacin, norfloxacin, ofloxacin, sparfloxacin, trovafloxacin, bacitracin, colistin, polymyxin B, sulfonamide, trimethoprim-sulfamethoxazole, co-amoxyclav, cephalothin, cefuroxime, ceftriaxone, vancomycin, gentamicin, amikacin, metronidazole, chloramphenicol, nitrofurantoin, co-trimoxazole, rifampicin, isoniazid, pyrazinamide, and the like;

Antiprotozoal agents include chloroquine, doxycycline, mefloquine, metronidazole, eplomithine, furazolidone, hydroxychloroquine, iodoquinol, pentamidine, mebendazole, piperazine, halofantrine, primaquine, pyrimethamine sulfadoxine, doxycycline, clindamycin, quinine sulfate, quinidine gluconate, quinine dihydrochloride, hydroxychloroquine sulfate, proguanil, quinine, clindamycin, atovaquone, azithromycin, suramin, melarsoprol, eflornithine, nifurtimox, amphotericin B, sodium stibogluconate, pentamidine isethionate, trimethoprim-sulfamethoxazole, pyrimethamine, sulfadiazine, and the like;

Antifungal agents include amphotericin B, fluconazole, itraconazole, ketoconazole, potassium iodide, flucytosine, and the like; and Antiproliferative agents such as altretamine, amifostine, anastrozole, arsenic trioxide, bexarotene, bleomycin, busulfan, capecitabine, carboplatin, carmustine, celecoxib, chlorambucil, cisplatin, cisplatin-epinephrine gel, cladribine, cytarabine liposomal, daunorubicin liposomal, daunorubicin daunomycin, dexrazoxane, docetaxel, doxorubicin, doxorubicin liposomal, epirubicin, estramustine, etoposide phosphate, etoposide VP-16, exemestane, fludarabine, fluorouracil 5-FU, fulvestrant, gemicitabine, gemtuzumab-ozogamicin, goserelin acetate, hydroxyurea, idarubicin, ifosfamide, imatinib mesylate, irinotecan, letrozole, leucovorin, levamisole, liposomal daunorubicin, melphalan L-PAM, mesna, methotrexate, methoxsalen, mitomycin C, mitoxantrone, paclitaxel, pamidronate, pegademase, pentostain, porfimer sodium, streptozocin, talc, tamoxifen, temozolamide, teniposide VM-26, topotecan, toremifene, tretinoin, ATRA, valrubicin, vinorelbine, zoledronate, and the like.

Anti-inflammatory agents include steroids such as predinsolone, corticosteroid, and the like.

A pharmaceutical or cosmetic formulation of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable co-solvent or combinations of co-solvents. Examples of suitable co-solvents include, but are not limited to, alcohol, propylene glycol, polyethylene glycol 300, polysorbate 80, glycerin and the like in concentrations ranging from about 0% to about 60% of the total volume.

The pharmaceutical formulation may also be in the form of a solution of a salt form of the active ingredient in an appropriate aqueous vehicle such as water or isotonic saline or dextrose solution.

The pharmaceutical formulations of the invention may be manufactured in manners generally known for preparing pharmaceutical compositions, e.g., using conventional techniques such as mixing, dissolving, granulating, drageemaking, levigating, emulsifying, encapsulating, entrapping or lyophilizing. Pharmaceutical formulations may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds of the present invention can be formulated readily by combining with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (compound), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally comprise gum horoi, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compounds and agents.

Pharmaceutical formulations which can be used orally include push-fit capsules made of gelatin, as well as soft, sealed capsules made of gelatin and a plasticizer, such as glycerol or sorbitol. The push-fit capsules can comprise the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the formulations may take the form of tablets or lozenges formulated in conventional manner.

Oral formulations generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral formulations can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can comprise any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Preferred formulations for oral formulations include microcrystalline tablets, gelatin capsules, or the like.

For administration intranasally or by inhalation, the compounds of the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated comprising a powder mix of the compound and a suitable powder base such as lactose or starch.

The compounds of the present invention may be formulated for parenteral administration by injection, e.g., by bolus injection or continuous infusion. Formulations for injection may be presented in unit-dosage form, e.g., in ampoules or in multi-dose containers, with an added preservative. The formulations may take such forms as suspensions, solutions or emulsions in oily or aqueous vehicles, and may comprise formulatory agents such as suspending, stabilizing and/or dispersing agents.

Pharmaceutical formulations suitable for injectable use include sterile aqueous solutions (where water soluble) or dispersions and sterile powders for the extemporaneous preparation of sterile injectable solutions or dispersion. Aqueous injection suspensions may comprise substances which increase the viscosity of the suspension, such as sodium carboxymethyl cellulose, sorbitol, or dextran. Optionally, the suspension may also comprise suitable stabilizers or agents which increase the solubility of the compounds to allow for the preparation of highly concentrated solutions. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes.

For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium comprising, for example, water, ethanol, polyol (for example, glycerol, propylene glycol, and liquid horoidsene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the formulation. Prolonged absorption of the injectable compositions can be brought about by including in the formulation an agent which delays absorption, for example, aluminum monostearate and gelatin.

Sterile injectable solutions can be prepared by incorporating a therapeutically effective amount of at least one compound of the present invention in an appropriate solvent with one or a combination of ingredients enumerated above, as required, followed by filtered sterilization. Generally, dispersions are prepared by incorporating the compound of the present invention into a sterile vehicle which comprises a basic dispersion medium and the required other ingredients from those enumerated above. In the case of sterile powders for the preparation of sterile injectable solutions, the preferred methods of preparation are vacuum drying and freeze-drying which yields a powder of the active compound plus any additional desired ingredient from a previously sterile-filtered solution thereof.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, foams, powders, sprays, aerosols or creams as generally known in the art.

For example, for topical formulations, pharmaceutically acceptable excipients or cosmetically acceptable carriers and additives include solvents, emollients, humectants, preservatives, emulsifiers, and pH agents. Suitable solvents include ethanol, acetone, glycols, polyurethanes, and others known in the art. Suitable emollients include petrolatum, mineral oil, propylene glycol dicaprylate, lower fatty acid esters, lower alkyl ethers of propylene glycol, cetyl alcohol, cetostearyl alcohol, stearyl alcohol, stearic acid, wax, and others known in the art. Suitable humectants include glycerin, sorbitol, and others known in the art. Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, propylene glycol stearate, and others known in the art. Suitable pH agents include hydrochloric acid, phosphoric acid, diethanolamine, triethanolamine, sodium hydroxide, monobasic sodium phosphate, dibasic sodium phosphate, and others known in the art. Suitable preservatives include benzyl alcohol, sodium benzoate, parabens, and others known in the art.

For administration to the eye, the compounds of the present invention of the present invention may delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, horoids/retina and selera. The pharmaceutically acceptable ophthalmic vehicle may be an ointment, vegetable oil, or an encapsulating material. Compounds of the present invention may also be injected directly into the vitreous and aqueous humor.

Alternatively, compounds of the present invention may be in powder form for constitution with a suitable vehicle, e.g., sterile pyrogen-free water, before use. The compounds of the present invention may also be formulated in rectal compositions such as suppositories or retention enemas, e.g., comprising conventional suppository bases such as cocoa butter or other glycerides.

In addition to the formulations described above, compounds of the present invention may also be formulated as a depot preparation. Such long-acting formulations may be administered by implantation (for example, subcutaneously or intramuscularly) or by intramuscular injection. Thus, for example, the compounds of the present invention may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) comprises VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied, for example: other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical formulations may be employed. Liposomes and emulsions are known examples of delivery vehicles or carriers for hydrophobic drugs and cosmetics. Certain organic solvents such as dimethylsulfoxide also may be employed, although usually at the cost of greater toxicity. Additionally, the compounds may be delivered using a sustained-release system, such as semipermeable matrices of solid hydrophobic polymers comprising the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical formulations also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, and the like. Salts tend to be more soluble in aqueous or other protonic solvents than are the corresponding free-base forms.

In one embodiment, the compounds of the present invention are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically or cosmetically acceptable carriers. These can be prepared according to methods known to those skilled in the art, for example, as described in U.S. Pat. No. 4,522,811.

It is especially advantageous to formulate oral or parenteral formulations in dosage unit form for ease of administration and uniformity of dosage. Dosage unit form as used herein refers to physically discrete units suited as unitary dosages for the subject to be treated; each unit comprising a predetermined quantity of active compound calculated to produce the desired therapeutic effect in association with the required pharmaceutical carrier.

The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The following Examples are intended to illustrate but not to limit the invention. In the following Examples, the compounds having the structural formulas in the above-referenced Schemes are referenced.

EXAMPLE 1

Sporozoite Induced Test in Mouse

The causal prophylactic antimalarial activity of the new carbamate derivatives were assessed in a sporozoites challenged mouse model according to the following protocol and the results are shown in Table 4 and Table 5.

A. Preparation of Compounds:

Each compound was ground with a mortar and pestle and suspended in 0.5% hydroxyethylcellulose and 0.1% Tween 80 for compounds to be administered PO and those given SC were suspended in peanut oil. Each compound is prepared at 3 different dose levels.

B. Administration of Compounds

Compounds were administered either PO or SC to mice once 4 hours before inoculation of sporozoites.

C. Animal Host

Four-week-old male CD-1 mice, purchased from Charles River and weighing about 16 to about 17 grams were placed 5 per cage and allowed to acclimate for 4 days before being treated and then inoculated with sporozoites. They were fed food and water ad-lib and maintained at 76° F. with 12 hour light and 12 hour darkness. The cages and water bottles were changed biweekly. The mice are weighed on Days 0, 3 and 6 then biweekly when blood films were taken.

D. Parasite Line

*Plasmodium yoelii* (17x) was used to infect mice that will be used to infect the mosquitoes.

E. Test Procedure

Mice were given a single dose of test compound 4 hours before being inoculated intraperitoneally with $2.5 \times 10^5$ sporozoites of *Plasmodium yoelii* on Day 0. Whole body weights were taken on Day 0 and Day 6 then twice a week for 31 days. A blood film was taken on Day 5 and then twice a week for 31 days. Mice loosing greater than about 20% of their body weight were sacrificed. All mice alive on Day 31 with no parasites in a blood film were considered cured. Donor mice used to infect the mosquitoes were infected with $2.5 \times 10^4$ parasitized erythrocytes. The mosquitoes were allowed to feed on these malaria-infected mice on Day 4 of their infection when the parasitemia was low.

F. Determination of Activity Against Either the Sporozoite or Exoerythrocytic (EE) Stage A compound was considered active against either the sporozoite or the EE stage if no parasites were found in the blood films taken on Day 5 or on subsequent blood films taken weekly for 31 days.

A compound was considered to exhibit marginal activity if only low levels of parasites were found (less than about 10%) in blood films taken on Day 5 or any biweekly for 31 days.

Mice alive on Day 31 with no parasites found in any blood films were considered cured.

TABLE 4

Minimum Protective Dose (mg/kg) Against *P. yoelii*

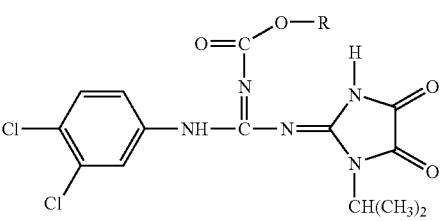

| Compound # | R | Dose |
|---|---|---|
| 3 | —H | >160 |
| 3a | —CH$_2$CH$_3$ | 2.5 |
| 3b | —CH$_2$CH(CH$_3$)CH$_3$ | >40 |
| 3c | —C(CH$_3$)$_3$ | 40 |
| 3d | —CH$_2$—C$_6$H$_5$ | >160 |

TABLE 4-continued

Minimum Protective Dose (mg/kg) Against *P. yoelii*

[Structure: 3,4-dichlorophenyl-NH-C(=N-)N=C with carbamate O-C(=O)-O-R and imidazolidinedione bearing CH(CH$_3$)$_2$]

| Compound # | R | Dose |
|---|---|---|
| 3e | —CH$_2$CH$_2$CH$_2$CH$_2$CH$_2$CH$_3$ | 40 |
| 3f | —CH$_2$-(4,5-dimethyl-1,3-dioxol-2-one-yl) | >40 |
| 3g | —CH$_2$CH$_2$CH=CHCH$_3$ (pentenyl) | 160 |
| 3h | —CH$_2$CH$_2$—O—CH$_2$—phenyl | 160 |
| Tafenoguine | | 2.5 |
| Primaquine | | 40 |
| Dihyroartemisinin | | 160 |

TABLE 5

Minimum Protective Dose (mg/kg) Against *P. yoelii*

[Structure: 3,4-dichlorophenyl-hydantoin with =N-C(NHCH(CH$_3$)$_2$)=N-C(=O)-O-R]

| Compound # | R | Dose |
|---|---|---|
| 4 | —H | 5 |
| 4a | —CH$_2$CH$_3$ | 5 |
| 4b | —CH$_2$CH(CH$_3$)$_2$ (CH$_2$CH with two CH$_3$) | 2.5 |

TABLE 5-continued

Minimum Protective Dose (mg/kg) Against *P. yoelii*

[Same structure as above]

| Compound # | R | Dose |
|---|---|---|
| 4c | —C(CH$_3$)$_3$ | 1.25 |
| 4d | —CH$_2$-phenyl | 10 |
| 4e | —CH$_2$CH$_2$CH$_2$CH$_2$CH$_2$CH$_3$ | 5 |
| 4g | pentenyl | — |
| Tafenoguine | | 2.5 |
| Primaguine | | 40 |
| Dihyroartemisinin | | 160 |

EXAMPLE 2

Causal Prophylactic Assay for Intramuscular Administration in Rhesus Monkey

In order to study the causal prophylactic activity of the 2-guanidinylimidazolidinedione compounds of the present invention, the following assay was conducted. Twelve rhesus monkeys were issued. The monkeys were randomized to 2 control animals and 5 groups of 2 experimental animals each. The groupings, 2-guanidinylimidazolidinedione compounds tested, dosages and routes of administration are shown in the following Table 6:

A donor monkey was inoculated intravenously with 1.3 ml, freshly-thawed frozen infected red blood cells (DA310). The experiments were conducted in US Army oversea laboratory, AFRIMS, Bankoku, Thailand. When the donor monkey developed gametocytemia, mosquito feedings were conducted on days 13 and 14 after inoculation. The donor monkey was treated with intramuscular chloroquine hydrochloride (CQ) 10 mg/kg, once a day after the second mosquito feeding and continued for 7 days.

On day 0 (beginning of assay), each of the 12 monkeys was inoculated intravenously with 1-ml inoculum of suspension containing about $1.0 \times 10^6$ *P. cynomolgi* sporozoites harvested from *Anopheles dirus* mosquitoes' salivary glands previously fed on the donor monkey. See Corcoran, K D, et al. (1993) Am. J. Trop. Med. Hyg. 49:473–477, and Shanks, G D, et al. (2001) Clinical Infectious Diseases 33:1968–1974, which are herein incorporated by reference.

TABLE 6

| Group | Monkey numbers | Testing Compound | Dosages (mg/kg) | Route |
|---|---|---|---|---|
| Control | DA889 DA891 | None (DMSO) | 0 | IM |
| Experimental Group 1 | DA888 DA895 | WR182393 | 30 | IM |
| Experimental Group 2 | DA874 DA894 | 4b | 30 | IM |

TABLE 6-continued

| Group | Monkey numbers | Testing Compound | Dosages (mg/kg) | Route |
|---|---|---|---|---|
| Experimental Group 3 | DA880 DA883 |  | 10 | IM |
| Experimental Group 4 | DA873 DA877 | 3c | 30 | IM |
| Experimental Group 5 | DA875 DA878 |  | 10 | IM |

The solubility and characteristics of the 2-guanidinylimidazolidinedione compounds tested are shown in the following Table 7:

TABLE 7

| Drug # | Dosage (mg/kg) | Vehicle | Solubility | Supernatant | Sediment |
|---|---|---|---|---|---|
| none | 0 | DMSO | N/A | Clear | None |
| WR182393 | 30 |  | Moderate | Yellow turbid | None |
| 4b | 30 |  | Low to Moderate | Clear | White light sediment |
|  | 10 |  | Good | Clear | None |
| 3c | 30 |  | Good | Yellow, clear | None |
|  | 10 |  | Good | Yellow, clear | None |

All monkeys received treatment on days −1, 0 and 1. The control monkeys received dimethylsulfoxide (DMSO) and the experimental animals received testing compound intramusculary.

All control monkeys showed positive parasitemia on day 9 after sporozoite inoculation, thereby validating the assay. Six monkeys (DA898, DA908, DA831, DA913, DA881, DA882) showed positive parasitemia on day 9, the same day as the control. DA910, DA899, DA905 and DA856 showed positive parasitemia on days 9, 10, 10 and 11 respectively. Eight monkeys (DA873, DA874, DA875, DA877, DA878, DA883, DA894, and DA895) remained parasite-free throughout 101 days after treatment.

After the assay, all monkeys were given standard malarial treatment. Specifically, seven-day primaquine (1.78 mg/kg) and chloroquine (10 mg/kg) were administered to treat all monkeys, 2 control and 12 experimental monkeys. As shown in the following Table 8:

TABLE 8

| Monkey No. | Group | Drug | Day of Parasitemia | Result |
|---|---|---|---|---|
| DA889 | Control | None | 10 | Valid control |
| DA891 |  | (DMSO) | 13 | Valid control |
| DA888 | 1 | WR182393, 30 mg/kg | 75 | Delay the parasitemia |
| DA895 |  |  | Remain parasite free | Causal prophylaxis |
| DA874 | 2 | 4b, 30 mg/kg | Remain parasite free | Causal prophylaxis |
| DA894 |  |  |  |  |
| DA880 | 3 | 4b, 10 mg/kg | 47 | Delay the parasitemia |
| DA883 |  |  | Remain parasite free | Causal prophylaxis |
| DA873 | 4 | 3c, 30 mg/kg | Remain parasite free | Causal prophylaxis |
| DA877 |  |  |  |  |
| DA875 | 5 | 3c, 10 mg/kg |  |  |
| DA878 |  |  |  |  |

Group 1, WR182393: The treatment regimen protected one monkey and delayed parasitemia in the other monkey for 62 days. This compound was previously tested and indicated causal prophylactic and radical curative activity. See Corcoran, K D (1993) Am. J. Med. Hyg. 49(4):473–477, which is herein incorporated by reference.

Groups 2 and 3, compound 4b: The two monkeys that received 30-mg/kg regimen were protected. The lower dose protected one monkey and delayed parasitemia in the other monkey for 34 days.

Groups 4 and 5, compound 3c: All four monkeys were protected.

EXAMPLE 3

Oral Causal Prophylactic Assay in Rhesus Monkey

To test the causal prophylactic intramuscular potency of the purified isomer of compound 3 and oral potency of two carbamate derivatives of 2-guanidinylimidazolidinedione (4b and 3c) the following assay was conducted.

Fourteen rhesus monkeys were issued. They were randomized into 7 groups of 2 animals each as provided in the following Table 9:

TABLE 9

| Group | Monkey numbers | Testing Compound | Dosages (mg/kg) | Route |
|---|---|---|---|---|
| Control, Group 1 | DA902 DA916 | None (HECT) | 0 | PO |
| Experimental Group 2 | DA900 DA923 | 3 | 30 | IM |
| Experimental Group 3 | DA898 DA908 |  | 10 | IM |
| Experimental Group 4 | DA831 DA913 | 4b | 30 | PO |

TABLE 9-continued

| Group | Monkey numbers | Testing Compound | Dosages (mg/kg) | Route |
|---|---|---|---|---|
| Experimental Group 5 | DA881 DA882 | | 10 | PO |
| Experimental Group 6 | DA856 DA905 | 3c | 30 | PO |
| Experimental Group 7 | DA899 DA910 | | 10 | PO |

A donor monkey was inoculated intravenously with 1.3 ml, freshly-thawed frozen infected red blood cell (DA310). When the monkey developed gametocytemia, mosquito feedings were conducted on days 15 and 16 after inoculation. The donor monkey was treated with intramuscular chloroquine hydrochloride (CQ) 10 mg/kg, once a day after the second mosquito feeding and continued for 6 days.

On day 0 of the beginning of the assay, each of the 14 monkeys was inoculated intravenously with 1-ml inoculum of suspension containing about $1.0 \times 10^6$ P. cynomolgi sporozoites harvested from Anopheles dirus mosquitoes' salivary glands previously fed on the donor monkey.

The solubility and characteristics of the 2-guanidinylimidazolidinedione compounds tested are shown in the following Table 10:

TABLE 10

| Drug # | Dosage (mg/kg) | Vehicle | Solubility | Supernatant | Sediment |
|---|---|---|---|---|---|
| None | 0 | HECT | N/A | Clear | None |
| 3 | 30 | DMSO | Moderate | Yellow turbid | None |
| | 10 | DMSO | Good | Yellow clear | None |
| 4b | 30 | HECT | Moderate | Turbid | White sediment |
| | 10 | HECT | Moderate | Turbid | White sediment |
| 3c | 30 | HECT | Moderate | Turbid | Yellow sediment |
| | 10 | HECT | Moderate | Turbid | Yellow sediment |

All monkeys received treatment on days −1, 0 and 1. The control monkeys (Group 1) received HECT orally and the experimental animals received testing compound intramuscularly (Groups 2 and 3) or orally (Groups 4 to 7).

Both control monkeys showed positive parasitemia on day 9, thereby validating the assay. Six monkeys (Groups 3 to 5) showed positive parasitemia on the same day as the control monkeys. Six monkeys (DA910, DA899, DA905, DA856, DA923 and DA900) were positive later on days 9, 10, 10, 11, 15 and 20 days after sporozoite inoculation, respectively.

After the assay, all monkeys were given standard malarial treatment. Specifically, seven-day primaquine (1.78 mg/kg) and chloroquine (10 mg/kg) were administered to treat all monkeys. As shown in the following Table 11:

TABLE 11

| Group | Monkey numbers | Testing Compound | Dosages (mg/kg) | Route | Day of Parasitemia | Result |
|---|---|---|---|---|---|---|
| 1 | DA902 | None (HECT) | 0 | PO | 8 | Valid control |
| | DA916 | | | | 8 | Valid control |
| 2 | DA900 | 3 | 30 | IM | 20 | 12 days Delay the parasitemia |
| | DA923 | | | | 15 | 7 days Delay the parasitemia |
| 3 | DA898 | | 10 | IM | 8 | No activity |
| | DA908 | | | | 8 | No activity |
| 4 | DA831 | 4b | 30 | PO | 8 | No activity |
| | DA913 | | | | 8 | No activity |
| 5 | DA881 | | 10 | PO | 8 | No activity |
| | DA882 | | | | 8 | No activity |
| 6 | DA856 | 3c | 30 | PO | 11 | 3 days Delay the parasitemia |
| | DA905 | | | | 10 | 2 days Delay the parasitemia |
| 7 | DA899 | | 10 | PO | 10 | 2 days Delay the parasitemia |
| | DA910 | | | | 9 | 1 days Delay the parasitemia |

Group 1, the two control monkeys became parasitemic 8 days after sporozoite inoculation, thereby validating the assay.

Group 2, compound 3 (30 mg/kg, i.m.): The parasite presented in 2 monkeys (DA923 and DA900) at 15 and 20 days after the inoculation, respectively. The compound did not completely protect the monkeys from malaria but delayed parasitemia for 7 and 12 days, respectively. This purified derivative contains partial exoerythrocytic activity to delay development of malaria in the 2 rhesus monkeys used in this experiment.

It is noted that when compared to WR182393 that showed causal prophylactic and radical curative activity, this purified compound at 30 mg/kg intramuscularly was less active. See Corcoran, K D (1993) Am. J. Med. Hyg. 49(4):473–477, which is herein incorporated by reference. Therefore, higher dosages of the purified derivative are preferred to increase the prophylactic efficacy.

Group 3, compound 3 (10 mg/kg, i.m.): The two monkeys were not protected.

Groups 4 and 5, compound 4b (30 and 10 mg/kg, p.o.): All four monkeys were not protected. As provided in Example 1, this compound at the same dosages showed partial to complete prophylactic activity when given intramuscularly. Therefore, the preferred route of administration is intramuscularly.

Groups 6 and 7, compound 3c (30 and 10 mg/kg, p.o.): The lower dose delayed parasitemia to days 9 and 10 after the inoculation and the higher dose delayed the parasitemia to days 10 and 11 after the inoculation. Although this compound caused a little increase in the prepatent period, but extension of the prepatent period corresponded with the increased dosage. Higher dosage may be required to increase the prophylactic efficacy.

As provided in Example 1, this compound at the same dosages showed complete prophylactic activity when given intramuscularly. Therefore, the preferred route of administration is intramuscularly.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A compound having the structural formula A or B

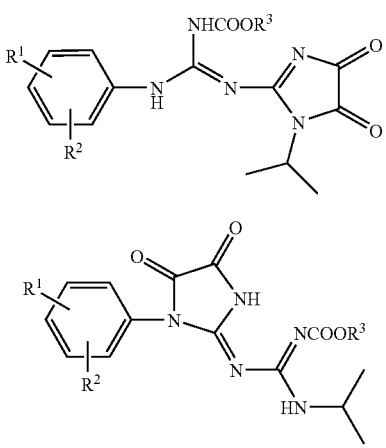

wherein $R^1$ and $R^2$ are each independently a hydrogen, halogen, substituted or unsubstituted alkyl, substituted or unsubstituted alkoxyl, amino, substituted or unsubstituted alkylamino or substituted or unsubstituted alkylaryl, and wherein $R^3$ is a substituted or unsubstituted alkyl, substituted or unsubstituted cycloalkyl, substituted or unsubstituted heterocycloalkyl, substituted or unsubstituted acyl, substituted or unsubstituted aryl, substituted or unsubstituted heteroaryl, substituted or unsubstituted alkylaryl, sulfonyl, or substituted or unsubstituted alkylsulfonyl, or a pharmaceutically acceptable salt thereof.

2. The compound of claim 1, wherein $R^1$ and $R^2$ are each independently —H, —Cl, —Br, —CF$_3$, —OCH$_3$, or —OCF$_3$.

3. The compound of claim 1, wherein $R^3$ is —CH$_2$CH$_3$, —CH$_2$CH(CH$_3$)$_2$, —C(CH$_3$)$_3$, —CH$_2$C$_6$H$_5$, —(CH$_2$)$_5$CH$_3$,

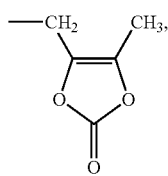

—CH$_2$CH$_2$C=CH$_2$, or —CH$_2$CH$_2$OCH$_2$C$_6$H$_5$.

4. A compound selected from the following group
N-(3,4-dichlorophenyl)-N'-(1-isopropyl-4,5-dioxoimidazolidin-2-ylidene)-guanidine (3);
N-(3,4-dichlorophenyl)-N'-ethoxycarbonyl-N"-(1-isopropyl-4,5-dioxo-imidazolidin-2-ylidene)-guanidine (3a);
N-(3,4-dichlorophenyl)-N'-(isobutoxycarbonyl)-N"-(1-isopropyl-4,5-dioxo-imidazolidin-2-ylidene)-guanidine (3b);
N-(3,4-dichlorophenyl)-N'-(1-isopropyl-4,5-dioxoimidazolidin-2-ylidene)-N"-(tert-butoxycarbonyl)-guanidine (3c);
N-(3,4-dichlorophenyl)-N'-(benzyloxycarbonyl)-N"-(1-isopropyl-4,5-dioxo-imidazolidin-2-ylidene)-guanidine (3d);
N-(3,4-dichlorophenyl)-N'-(1-hexyloxycarbonyl)-N"-(1-isopropyl-4,5-dioxo-imidazolidin-2-ylidene)-guanidine (3e);
N-(3,4-dichloro-phenyl)-N'-(5-methyl-2-oxo-1,3-dioxol-4-yl)methyl-N'-(1-isopropyl-4,5-dioxo-imidazolidin-2-ylidene)guanidine (3f);
N-(3,4-dichlorophenyl)-N'-(3-butenyloxycarbonyl)-N"-(1-isopropyl-4,5-dioxoimidazolidin-2-ylidene)-guanidine (3g);
N-(3,4-dichloro-phenyl)-N'-(2-benzyloxyethoxycarbonyl)-N"-(1-isopropyl-4,5-dioxo-imidazolidin-2-ylidene)-guanidine (3h);
N-[1-(3,4-dichlorophenyl)-4,5-dioxo-4,5-dihydro-1H-imidazol-2-yl]-N'-isopropylguanidine (4);
N-[1-(3,4-dichlorophenyl)-4,5-dioxo-imidazolidin-2-ylidene]-N'-isopropyl-N"-(ethylcarbonyl)guanidine (4a);
N-[1-(3,4-dichlorophenyl)-4,5-dioxo-imidazolidin-2-ylidene]-N'-isopropyl-N"-(isobutyloxycarbonyl)guanidine (4b);
N-[1-(3,4-dichlorophenyl)-4,5-dioxo-imidazolidin-2-ylidene]-N'-isopropyl-N"-(tert-butoxycarbonyl)guanidine (4c);
N-[1-(3,4-dichlorophenyl)-4,5-dioxo-imidazolidin-2-ylidene]-N'-isopropyl-N"-(benzyloxycarbonyl)guanidine (4d);
N-[1-(3,4-dichlorophenyl)-4,5-dioxo-imidazolidin-2-ylidene]-N'-isopropyl-N"-(1-hexyloxycarbonyl)guanidine (4e); and
N-[1-(3,4-dichlorophenyl)-4,5-dioxo-imidazolidin-2-ylidene]-N'-isopropyl-N"-(3-butenyloxycarbonyl) guanidine (4g).

5. A method of treating, preventing, or inhibiting malaria or a disease or disorder associated with malaria or a *Plasmodium* parasite which comprises administering a therapeutically effective amount of at least one compound of claim 1 to a subject in need thereof.

6. The method of claim 5, wherein $R^1$ and $R^2$ are each independently —H, —Cl, —Br, —CF$_3$, —OCH$_3$, or —OCF$_3$.

7. The method of claim 5, wherein $R^3$ is —CH$_2$CH$_3$, —CH$_2$CH(CH$_3$)$_2$, —C(CH$_3$)$_3$, —CH$_2$C$_6$H$_5$, —(CH$_2$)$_5$CH$_3$,

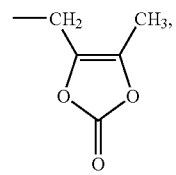

—CH$_2$CH$_2$C=CH$_2$, or —CH$_2$CH$_2$OCH$_2$C$_6$H$_5$.

8. The method of claim 5, wherein the compound is administered intramuscularly, orally, or transdermally.

9. A method of treating, preventing, or inhibiting malaria or a disease or disorder associated with malaria or a *Plasmodium* parasite which comprises administering to a subject in need thereof a therapeutically effective amount of at least one compound selected from the following group N-(3,4-dichlorophenyl)-N'-ethoxycarbonyl-N''-(1-isopropyl-4,5-dioxo-imidazolidin-2-ylidene)-guanidine (3a);

N-(3,4-dichlorophenyl)-N'-(isobutoxycarbonyl)-N''-(1-isopropyl-4,5-dioxo-imidazolidin-2-ylidene)-guanidine (3b);

N-(3,4-dichlorophenyl)-N'-(1-isopropyl-4,5-dioxoimidazolidin-2-ylidene)-N''-(tert-butoxycarbonyl)-guanidine (3c);

N-(3,4-dichlorophenyl)-N'-(benzyloxycarbonyl)-N''-(1-isopropyl-4,5-dioxo-imidazolidin-2-ylidene)-guanidine (3d);

N-(3,4-dichlorophenyl)-N'-(1-hexyloxycarbonyl)-N''-(1-isopropyl-4,5-dioxo-imidazolidin-2-ylidene)-guanidine (3e);

N-(3,4-dichloro-phenyl)-N'-(5-methyl-2-oxo-1,3-dioxol-4-yl)methyl-N''-(1-isopropyl-4,5-dioxo-imidazolidin-2-ylidene)guanidine (3f);

N-(3,4-dichlorophenyl)-N'-(3-butenyloxycarbonyl)-N''-(1-isopropyl-4,5-dioxoimidazolidin-2-ylidene)-guanidine (3g);

N-(3,4-dichloro-phenyl)-N'-(2-benzyloxyethoxycarbonyl)-N''-(1-isopropyl-4,5-dioxo-imidazolidin-2-ylidene)-guanidine (3h);

N-[1-(3,4-dichlorophenyl)-4,5-dioxo-4,5-dihydro-1H-imidazol-2-yl]-N'-isopropylguanidine (4);

N-[1-(3,4-dichlorophenyl)-4,5-dioxo-imidazolidin-2-ylidene]-N'-isopropyl-N''-(ethylcarbonyl)guanidine (4a);

N-[1-(3,4-dichlorophenyl)-4,5-dioxo-imidazolidin-2-ylidene]-N'-isopropyl-N''-(isobutyloxycarbonyl)guanidine (4b);

N-[1-(3,4-dichlorophenyl)-4,5-dioxo-imidazolidin-2-ylidene]-N'-isopropyl-N''-(tert-butoxycarbonyl)guanidine (4c);

N-[1-(3,4-dichlorophenyl)-4,5-dioxo-imidazolidin-2-ylidene]-N'-isopropyl-N''-(benzyloxycarbonyl)guanidine (4d);

N-[1-(3,4-dichlorophenyl)-4,5-dioxo-imidazolidin-2-ylidene]-N'-isopropyl-N''-(1-hexyloxycarbonyl)guanidine (4e); and N-[1-(3,4-dichlorophenyl)-4,5-dioxo-imidazolidin-2-ylidene]-N'-isopropyl-N''-(3-butenyloxycarbonyl)guanidine (4g).

10. The method of claim 9, and further comprising administering to the subject a supplementary active compound.

11. The method of claim 10, wherein the supplementary active compound is an antimalarial, an antiproliferative agent, an antifungal agent, an antibacterial, or an anti-inflammatory agent.

12. The method of claim 9, wherein the compound is

N-(3,4-dichlorophenyl)-N'-ethoxycarbonyl-N''-(1-isopropyl-4,5-dioxo-imidazolidin-2-ylidene)-guanidine (3a);

N-(3,4-dichlorophenyl)-N'-(1-isopropyl-4,5-dioxoimidazolidin-2-ylidene)-N''-(tert-butoxycarbonyl)-guanidine (3c);

N-[1-(3,4-dichlorophenyl)-4,5-dioxo-imidazolidin-2-ylidene]-N'-isopropyl-N''-(ethylcarbonyl)guanidine (4a);

N-[1-(3,4-dichlorophenyl)-4,5-dioxo-imidazolidin-2-ylidene]-N'-isopropyl-N''-(isobutyloxycarbonyl)guanidine (4b); or N-[1-(3,4-dichlorophenyl)-4,5-dioxo-imidazolidin-2-ylidene]-N'-isopropyl-N''-(tert-butoxycarbonyl)guanidine (4c).

13. The method of claim 9, and further comprising administering a therapeutically effective amount of N-(3,4-dichlorophenyl)-N'-(1-isopropyl-4,5-dioxoimidazolidin-2-ylidene)guanidine (3).

14. A method for making N-(3,4-dichlorophenyl)-N'-(1-isopropyl 4,5-dioxoimidazolidin-2-ylidene)guanidine (3) which comprises reacting N-(3,4-dichlorophenyl)guanidine (14) with 1-isopropyl-2-methylsulfanyl-1H-imidazole-4,5-dione (11).

15. The method of claim 14, which further comprises preparing N-(3,4-dichlorophenyl)guanidine (14) by adding NH$_4$OH to 1-(3,4-dichlorophenyl)-2-methyl-isothiourea (13) in ethanol to obtain a solution, refluxing the solution, removing the solvent to obtain a residue, and obtaining N-(3,4-dichlorophenyl)guanidine (14).

16. The method of claim 14, which further comprises preparing 1-isopropyl-2-methylsulfanyl-1H-imidazole-4,5-dione (11) by adding iodomethane to isopropyl thiourea in dry acetone, obtaining the hydroiodide salt, obtaining a suspension of the hydroiodide salt, adding triethylamine to the suspension, adding oxalyl chloride to the suspension, and obtaining 1-isopropyl-2-methylsulfanyl-1H-imidazole-4,5-dione (11) by crystallization.

17. A method for making the compound having the structural formula A of claim 1, which comprises treating a compound having the structural formula a

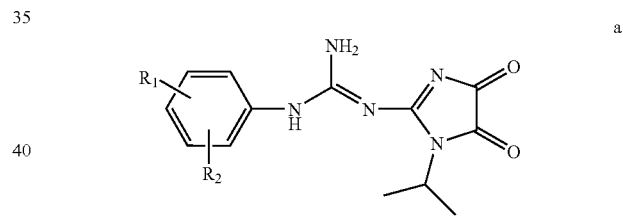

with an alkyl chloroformate having the structural formula x

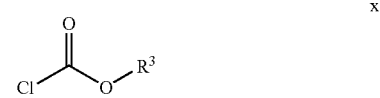

under the catalysis of triethylamine or a dialkyldicarbonate having the structural formula y

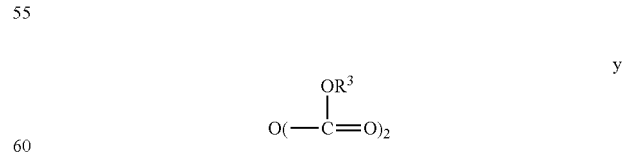

under the catalysis of dimethylaminopyridine (DMAP), wherein $R^1$ and $R^2$ are each independently a hydrogen, halogen, substituted or unsubstituted alkyl, substituted or unsubstituted alkoxyl, amino, substituted or unsubstituted alkylamino or substituted or unsubstituted aralkyl, and wherein R³ is a substituted or unsubstituted alkyl, substituted or unsubstituted cycloalkyl, substituted or unsubstituted heterocycloalkyl, substituted or unsubstituted acyl, substituted or unsubstituted aryl, substituted or unsubstituted heteroaryl, substituted or unsubstituted alkylaryl, sulfonyl, or substituted or unsubstituted alkylsulfonyl.

18. The method of claim 17, wherein R¹ and R² are each independently —H, alkyl, —Cl, —Br, —CF₃, —OCH₃, or —OCF₃.

19. The method of claim 17, wherein R³ is —CH₂CH₃, —CH₂CH(CH₃)₂, —C(CH₃)₃, —CH₂C₆H₅, —(CH₂)₅CH₃,

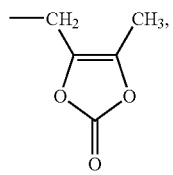

—CH₂CH₂C=CH₂, or —CH₂CH₂OCH₂C₆H₅.

20. A method for making N-[1-(3,4-dichlorophenyl)-4,5-dioxo-4,5-dihydro-1H-imidazol-2-yl]-N'-isopropyl-guanidine (4) which comprises
    reacting 1-(3,4-dichlorophenyl)-2-methylsulfanyl-1H-imidazole-4,5-dione (15) with isopropylguanidine, or
    acid hydrolysis of N-[1-(3,4-dichlorophenyl)-4,5-dioxo-imidazolidin-2-ylidene]-N'-isopropyl-N''-(tert-butoxycarbonyl)guanidine (4c).

21. The method of claim 20, wherein N-[1-(3,4-dichlorophenyl)-4,5-dioxo-imidazolidin-2-ylidene]-N'-isopropyl-N''-(tert-butoxycarbonyl)guanidine (4c) is prepared by reacting 1-(3,4-dichlorophenyl)-2-methylsulfanyl-1H-imidazole-4,5-dione (15) with N-isopropyl-N'-(tert-butoxycarbonyl)guanidine.

22. The method of claim 20, wherein 1-(3,4-dichlorophenyl)-2-methylsulfanyl-1H-imidazole-4,5-dione (15) is prepared by adding methyl oxalyl chloride to a solution of 1-(3,4-dichlorophenyl)-2-methylisothiourea (13) and triethylamine in dry CH₂Cl₂.

23. The method of claim 21, wherein N-isopropyl-N'-(tert-buyloxycarbonyl)guanidine is obtained by adding a solution of di-tert-butyl dicarbonate in CHCl₃ to a solution of isopropylguanidine in DMF.

24. A method for making the compound having the structural formula B of claim 1, which comprises treating a compound having the structural formula b

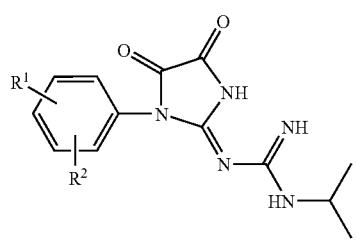

with an alkyl chloroformate having the structural formula x

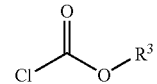

under the catalysis of triethylamine or a dialkyldicarbonate having the structural formula y

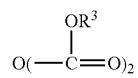

under the catalysis of dimethylaminopyridine (DMAP),
    wherein R¹ and R² are each independently a hydrogen, halogen, substituted or unsubstituted alkyl, substituted or unsubstituted alkoxyl, amino, substituted or unsubstituted alkylamino or substituted or unsubstituted aralkyl, and
    wherein R³ is a substituted or unsubstituted alkyl, substituted or unsubstituted cycloalkyl, substituted or unsubstituted heterocycloalkyl, substituted or unsubstituted acyl, substituted or unsubstituted aryl, substituted or unsubstituted heteroaryl, substituted or unsubstituted alkylaryl, sulfonyl, or substituted or unsubstituted alkylsulfonyl.

25. The method of claim 24, wherein R¹ and R² are each independently —H, —Cl, —Br, —CF₃, —OCH₃, or —OCF₃.

26. The method of claim 24, wherein R³ is —CH₂CH₃, —CH₂CH(CH₃)₂, —C(CH₃)₃, —CH₂C₆H₅, —(CH₂)₅CH₃,

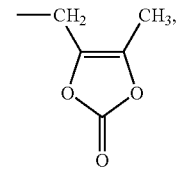

—CH₂CH₂C=CH₂, or —CH₂CH₂OCH₂C₆H₅.

27. A pharmaceutical composition comprising at least one compound of claim 1 and a pharmaceutically acceptable excipient.

28. The pharmaceutical composition of claim 27, wherein R¹ and R² are each independently —H, —Cl, —Br, —CF₃, —OCH₃, or —OCF₃.

29. The pharmaceutical composition of claim 27, wherein R³ is —CH₂CH₃, —CH₂CH(CH₃)₂, —C(CH₃)₃, —CH₂C₆H₅, —(CH₂)₅CH₃,

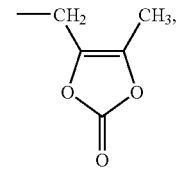

—CH₂CH₂C=CH₂, or —CH₂CH₂OCH₂C₆H₅.

30. A pharmaceutical composition comprising at least one compound of claim 4 and a pharmaceutically acceptable axcipient.

31. The pharmaceutical composition of claim 30, and further comprising a supplementary active compound.

32. The pharmaceutical composition of claim 31, wherein the supplementary active compound is an antimalarial, an antiproliferative agent, an antifungal agent, an antibacterial, or an anti-inflammatory agent.

33. The pharmaceutical composition of claim 30, and further comprising N-(3,4-dichlorophenyl)-N'-(1-isopropyl-4,5-dioxoimidazolidin-2-ylidene)guanidine (3).

34. A kit comprising at least one compound of claim 4 packaged together with instructional material.

* * * * *